United States Patent [19]
Noteborn et al.

[11] Patent Number: 5,981,502
[45] Date of Patent: Nov. 9, 1999

[54] METHODS AND COMPOSITIONS FOR INDUCING APOPTOSIS IN TUMOR CELLS

[75] Inventors: Matheus Hubertus Maria Noteborn, Leiderdorp; Guus Koch, AG Lelystad, both of Netherlands

[73] Assignee: Leadd B.V., Netherlands

[21] Appl. No.: 08/485,001

[22] Filed: Jun. 7, 1995

Related U.S. Application Data

[63] Continuation-in-part of application No. 08/030,335, Mar. 8, 1993, Pat. No. 5,491,073.

[30] Foreign Application Priority Data

Sep. 12, 1990 [NL] Netherlands ............................ 9002008
Jul. 20, 1993 [NL] Netherlands ............................ 9301272

[51] Int. Cl.$^6$ .......................... A61K 38/00; A01N 43/04; A01N 37/08; G01N 33/574
[52] U.S. Cl. .................................. 514/44; 514/12; 514/2; 435/7.23
[58] Field of Search .............................. 424/204.1, 184.1, 424/186.1; 514/44, 12, 2; 435/7.23

[56] References Cited

U.S. PATENT DOCUMENTS 5,554,525  9/1996  Sondermeijer et al. ................. 435/349

FOREIGN PATENT DOCUMENTS 0483911  5/1992  European Pat. Off. .
0533294  3/1993  European Pat. Off. .

OTHER PUBLICATIONS

Dermer. "Another anniversary for the wasr on cancer" Bio/technology. vol. 12, p. 320 Mar. 12, 1994.

Orkin et al. "Report and recommendations of the panel to assess the NIH investment in research on gene therapy" Dec. 7, 1995.

Zhuang et al, "Apoptin, a protein derived from chicken anemia virus, induces p53–independent apoptosis in human osteosarcoma cells" Cancer Research, vol. 55, p. 486–489 Feb. 1, 1995.

Zhuang et al, "Differential sensitivity to Ad5 E1B–21kD and bcl–2 proteins of apoptin–induced versus p53–induced apoptosis" Carcinogenesis, vol. 16/12, p. 2939–2944 1995.

Zhuang et al, "Apoptin, a protein encoded by chicken anemia virus, induces cell death in various human hematologic malignant cells in vitro" Leukemia, vol. 9 suppl 1, p. 118–120 1995.

Gelderblom et al., (1989) Archives of Virol. 109: 115–120.

Jeurissen et al., (1992) J. Virol. 66: 7383–7388.

Noteborn et al., (1991) J. Virol. 65: 3131–3139.

Noteborn et al., (1992a) Gene 118: 267–271.

Noteborn et al., (1993) In: Vaccines '93 CSHL Press. Cold Spring Harbor, USA. P. 299–304.

Noteborn et al., (1992b) Avian Pathology 21: 107–118.

Todd et al., (1990) J. Gen. Virology 71: 819–823.

Todd et al., (1991) Arch Virol. 117: 129–135.

*Primary Examiner*—Sheela Huff
*Assistant Examiner*—Yvonne Eyler
*Attorney, Agent, or Firm*—Barbara Rae-Venter; Rae-Venter Law Group, P.C.

[57] ABSTRACT

Novel proteins of the Chicken Anemia Virus are described and compositions for preventing or treating infections with that virus (CAV), in particular vaccines less pathogenic than the CAV itself, but yet leading to neutralizing antibodies in the immunized animal. Besides, there are described compositions containing antibodies against parts of the CAV for the control of infections with CAV and anti-idiotype antibodies. The invention also provides antibodies and test kits for the detection of CAV. Recombinant DNA molecules derived from CAV and host cells transfected therewith and vaccines based on these host cells are made possible by this invention. The invention also comprises living virus vaccines in which apiece of DAN is brought into a virus infectious to the host. Besides, the Invention provides uses of proteins of CAV in the induction of apoptosis, in particular in tumor cells. It further provides the induction of cell death by means of gene therapy.

7 Claims, 17 Drawing Sheets

```
  M   A   R   R   A   R   R   P   R   G   R   F   Y   S   F   R   R   G   R   W
ATGGCAAGACGAGCTCGCAGA. CGAGAGGCCGATTTTACTCCTTCAGAAGA..CACGGTGG    912
  H   H   L   K   R   L   R   R   R : Y   K   F   R   H   R   R   R   Q   R   Y
CACCACCTCAAGCGACTTCGACGAAGATATAAATTTCGACATCGGAGGAGACAGCGGTAT    972
  R   R   R   A   F   R   K   A   F   H   N   P   R   P   G   T   Y   S   V   R
CGTAGACGAGCTTTTAGGAAGGCCTTTCACAACCCCCGCCCCGGTACGTATAGTGTGAGG   1032
  L   P   N   P   Q   S   T   M   T   I   R   F   Q   G   V   I   F   L   T   E
CTGCCGAACCCCCAATCTACTATGACTATCCGCTTCCAAGGGGTCATCTTTCTCACGGAA   1092
  G   L   I   L   P   K   N   S   T   A   G   G   Y   A   D   H   M   Y   G   A
GGACTCATTCTGCCTAAAAACAGCACAGCGGGGGCTATGCAGACCACATGTACGGGGCG    1152
  R   V   A   K   I   S   V   N   L   K   E   F   L   L   A   S   M   N   L   T
AGAGTCGCCAAGATCTCTGTGAACCTGAAAGAGTTCCTGCTAGCCTCAATGAACCTGACA   1212
  Y   V   S   K   I   G   G   P   I   A   G   E   L   I   A   D   G   S   K   S
TACGTGAGCAAAATCGGAGGCCCCATCGCCGGTGAGTTGATTGCGGACGGGTCTAAATCA   1272
  Q   A   A   D   N   W   P   N   C   W   L   P   L   D   N   N   V   P   S   A
CAAGCCGCGGACAATTGGCCTAATTGCTGGCTGCCGCTAGATAATAACGTGCCCTCCGCT   1332
  T   P   S   A   W   W   R   W   A   L   M   M   M   Q   P   T   D   S   C   R
ACACCATCGGCATGGTGGAGATGGGCCTTAATGATGATGCAGCCCACGGACTCTTGCCGG   1392
  F   F   N   H   P   K   Q   M   T   L   Q   D   M   G   R   M   F   G   G   W
TTCTTTAATCACCCAAAGCAGATGACCCTGCAAGACATGGGTCGCATGTTTGGGGGCTGG   1452
  H   L   F   R   H   I   E   T   R   F   Q   L   L   A   T   K   N   E   G   S
CACCTGTTCCGACACATTGAAACCCGCTTTCAGCTCCTTGCCACTAAGAATGAGGGATCC   1512
  F . S   P   V   A   S   L   L   S   Q   G   E   Y   L   T   R   R   D   D   V
TTCAGCCCCGTGGCGAGTCTTCTCTCCCAGGGAGAGTACCTCACGCGTCGGGACGATGTT   1572
  K   Y   S   S   D   H   Q   N   R   W   Q   K   G   G   Q   P   M   T   G   G
AAGTACAGCAGCGATCACCAGAACCGGTGGCAAAAAGGCGGACAACCGATGACGGGGGC   1632
  I   A   Y   A   T   G   K   M   R   P   D   E   Q   Q   Y   P   A   M   P   P
ATTGCTTATGCGACCGGGAAAATGAGACCCGACGAGCAACAGTACCCTGCTATGCCCCCA   1692
  D   P   P   I   I   T   A   T   T   A   Q   G   T   Q   V   R   C   M   N   S
GACCCCCCGATCATCACCGCTACTACAGCGCAAGGCACGCAAGTCCGCTGCATGAATAGC   1752
  T   Q   A   W   W   S   W   D   T   Y   M   S   F   A   T   L   T   A   L   G
ACGCAAGCTTGGTGGTCATGGGACACATATATGAGCTTTGCAACACTCACAGCACTCGGT   1812
  A   Q   W   S   F   P   P   G   Q   R   S   V   S   R   R   S   F   N   H   H
GCACAATGGTCTTTTCCTCCAGGGCAACGTTCAGTTTCTAGACGGTCCTTCAACCACCAC   1872
  K   A   R   G   A   G   D   P   K   G   Q   R   W   H   T   L   V   P   L   G
AAGGCGAGAGGAGCCGGGGACCCCAAGGGCCAGAGATGGCACACGCTGGTGCCGCTCGGC   1932
  T   E   T   I   T   D   S   Y   M   S   A   P   A   S   E   L   D   T   N   F
ACGGAGACCATCACCGACAGCTACATGTCAGCACCCGCATCAGAGCTGGACACTAATTTC   1992
  F   T   L   Y   V   A   Q   G   T   N   K   S   Q   Q   Y   K   F   G   T   A
TTTACGCTTTACGTAGCGCAAGGCACAAATAAGTCGCAACAGTACAAGTTCGGCACAGCT   2052
  T   Y   A   L   K   E   P   V   M   K   S   D   A   W   A   V   V   R   V   Q
ACATACGCGCTAAAGGAGCCGGTAATGAAGAGCGATGCATGGGCAGTGGTACGCGTCCAG   2112
  S   V   W   Q   L   G   N   R   Q   R   P   Y   P   W   D   V   N   W   A   N
TCGGTCTGGCAGCTGGGTAACAGGCAGAGGCCATACCCATGGGACGTCAACTGGGCGAAC   2172
  S   T   M   Y   W   G   T   Q   P   *
AGCACCATGTACTGGGGGACGCAGCCCTGA                                  2201
```

FIG. 1

```
      M   H   G   N   G   G   Q   P   A   A   G   G   S   E   S   A   L   S   R   E
ATGCACGGGAACGGCGGACAACCGGCCGCTGGGGGCAGTGAATCGGCGCTTAGCCGAGAG                              439
      G   Q   P   G   P   S   G   A   A   Q   G   Q   V   I   S   N   E   R   S   P
GGGCAACCTGGGCCCAGCGGAGCCGCGCAGGGGCAAGTAATTTCAAATGAACGCTCTCCA                              499
      R   R   Y   S   T   R   T   I   N   G   V   Q   A   T   N   K   F   T   A   V
AGAAGATACTCCACCCGGACCATCAACGGTGTTCAGGCCACCAACAAGTTCACGGCCGTT                              559
      G   N   P   S   L   Q   R   D   P   D   W   Y   R   W   N   Y   N   H   S   I
GGAAACCCCTCACTGCAGAGAGATCCGGATTGGTATCGCTGGAATTACAATCACTCTATC                              619
      A   V   W   L   R   E   C   S   R   S   H   A   K   I   C   N   C   G   Q   F
GCTGTGTGGCTGCGCGAATGCTCGCGCTCCCACGCTAAGATCTGCAACTGCGGACAATTC                              679
      R   K   H   W   F   Q   E   C   A   G   L   E   D   R   S   T   Q   A   S   L
AGAAAGCACTGGTTTCAAGAATGTGCCGGACTTGAGGACCGATCAACCCAAGCCTCCCTC                              739
      E   E   A   I   L   R   P   L   R   V   Q   G   K   R   A   K   R   K   L   D
GAAGAAGCGATCCTGCGACCCCTCCGAGTACAGGGTAAGCGAGCTAAAAGAAAGCTTGAT                              799
      Y   H   Y   S   Q   P   T   P   N   R   K   K   A   Y   K   T   V   R   W   Q
TACCACTACTCCCAGCCGACCCCGAACCGCAAAAAGGCGTATAAGACTGTAAGATGGCAA                              859
      D   E   L   A   D   R   E   A   D   F   T   P   S   E   E   D   G   T   T
GACGAGCTCGCAGACCGAGAGGCCGATTTTACTCCTTCAGAAGAGGACGGTGGCACCACC                              919
      S   S   D   F   D   E   D   I   N   F   D   I   G   G   D   S   G   I   V   D
TCAAGCGACTTCGACGAAGATATAAATTTCGACATCGGAGGAGACAGCGGTATCGTAGAC                              979
      E   L   L   G   R   P   F   T   T   P   A   P   V   R   I   V   *
GAGCTTTTAGGAAGGCCTTTCACAACCCCCGCCCCGGTACGTATAGTGTGA                                       1030
```

FIG. 2

```
  M   N   A   L   Q   E   D   T   P   P   G   P   S   T   V   F   R   P   P   T
ATGAACGCTCTCCAAGAAGATACTCCACCCGGACCATCAACGGTGTTCAGGCCACCAACA         545
  S   S   R   P   L   E   T   P   H   C   R   E   I   R   I   G   I   A   G   I
AGTTCACGGCCGTTGGAAACCCCTCACTGCAGAGAGATCCGGATTGGTATCGCTGGAATT         605
  T   I   T   L   S   L   C   G   C   A   N   A   R   A   P   T   L   R   S   A
ACAATCACTCTATCGCTGTGTGGCTGCGCGAATGCTCGCGCTCCCACGCTAAGATCTGCA         665
  T   A   D   N   S   E   S   T   G   F   K   N   V   P   D   L   R   T   D   Q
ACTGCGGACAATTCAGAAAGCACTGGTTTCAAGAATGTGCCGGACTTGAGGACCGATCAA         725
  P   K   P   P   S   K   K   R   S   C   D   P   S   E   Y   R   V   S   E   L
CCCAAGCCTCCCTCGAAGAAGCGATCCTGCGACCCCTCCGAGTACAGGGTAAGCGAGCTA         785
  K   E   S   L   I   T   T   T   P   S   R   P   R   T   A   K   R   R   I   R
AAAGAAAGCTTGATTACCACTACTCCCAGCCGACCCCGAACCGCAAAAAGGCGTATAAGA         845
  L   *
CTGTAA                                                                851
```

FIG. 3

Amino-Acid Sequence of VP3.

```
1 -M  N  A  L  Q  E  D  T  P  P  G  P  S  T  V
   F  R  P  P  T  S  S  R  P  L  E  T  P  H  C
   R  E  I  R  I  G  I  A  G  I  T  I  T  L  S
   L  C  G  C  A  N  A  R  P  T  L  R  S  A  D
   T  A  D  N  S  E  S  T  G  F  K  N  V  P  D
   L  R  T  D  Q  P  K  P  P  S  K  K  R  S  C
   D  P  S  E  Y  R  V  S  E  L  K  E  S  L  I
   T  T  T  P  S  R  P  R  T  A  K  R  R  I  R
   L -121
```

METHODS AND COMPOSITIONS FOR INDUCING APOPTOSIS IN TUMOR CELLS

CROSS-REFERENCE TO RELATED APPLICATIONS

This application is a continuation-in-part of U.S. application Ser. No. 08/454,121, filed Nov. 30, 1995, pending, which is the National Stage of International Application No. PCT/NL94/00168, which is a continuation-in-part of U.S. application Ser. No. 08/030,335 filed Mar. 8, 1993, which issued as U.S. Pat. No. 5,491,073, which is the National Stage of International Application No. PCT/NL91/00165, filed Sep. 11, 1991, which disclosures are hereby incorporated by reference.

INTRODUCTION

1. Technical Field

The invention relates to compositions and methods for inducing apoptosis in cancer cells. The method is exemplified by the use of chicken anemia viral protein VP3 to induce p53-independent apoptosis in human tumor cells.

2. Background

Normal human somatic cells display a finite replicative capacity of 50–100 population doubling characterized by a cessation of proliferation in spite of the presence of abundant growth factors. This cessation of replication in vitro is variously referred to as cellular senescence or cellular aging. The replicative life span of cells is inversely proportional to the in vivo age of the donor, and therefore cellular senescence is suggested to play an important role in aging in vivo.

Cellular immortalization (the acquisition of unlimited replicative capacity) may be thought of as an abnormal escape from cellular senescence. Normal human somatic cells appear to be mortal, i.e., have finite replicative potential. In contrast, the germ line and malignant tumor cells are immortal (have indefinite proliferative potential). Human cells cultured in vitro appear to require the aid of transforming viral oncoproteins to become immortal and even then the frequency of immortalization is $10^{-6}$ to $10^{-7}$.

Apoptosis is an active and programmed process for eliminating superfluous, altered or malignant cells, which can be initiated by a variety of environmental stimuli. One of the striking features of apoptosis is phagocytosis of apoptotic cells by their neighbors. Therefore, apoptosis causes much less destruction of tissue than necrosis, the non-physiological type of cell death.

There is evidence that inhibition of the apoptotic processes can be important in tumor formation. As a result, the elimination of tumor cells via induction of apoptotic cell death has become a promising approach in experimental cancer therapy. A variety of chemotherapeutic compounds and ionizing radiation have been demonstrated to induce apoptosis in tumor cells, in many instances via wild-type p53. Apoptosis is characterized by shrinkage of cells, segmentation of the nucleus, condensation and eventual internucleosomal degradation of DNA. An apoptotic pathway can be characterized by its mediator(s) assists represser(s). It has been shown that the tumor suppressor protein p53 can act as a positive regulator of apoptosis. (Over)expression of wild-type p53 can induce apoptosis in a number of cell types. In addition, p53 is required for the efficient induction of apoptotic death by a variety of signals. The adenovirus type 5 (Ad5) E1B-55kD protein appears to counteract the p53-dependent apoptotic pathway by binding to p53. The adenovirus E1B-21kD and proto-oncogene Bcl-2 counter a wide range of apoptotic stimuli, and seem to exert their anti-apoptotic action downstream of p53. Although E1B-21kD and Bcl-2 share functional homologies, and interact with a common set of cellular proteins, E1B-21kD can be more active than Bcl-2 in certain circumstances. Both E1B-21kD and Bcl-2 have been shown to repress p53-dependent as well as p53-independent pathways, which suggests that these pathways share common mediators that might be affected by both E1B-21kD and Bcl-2.

Subject to particular inducing agents or cellular backgrounds, the induction of apoptosis can also take place in a p53-independent manner. Unfortunately, a large number of tumors acquire a mutation in p53 during their development therapy. It therefore would be of interest to identify compositions and methods by which to induce p53-independent apoptosis as a means of inhibiting tumor cell growth.

3. Relevant Literature

Todd et al., (1990) *J. Gen. Virol.* 71:819–823 have shown that isolated CAV particles contain only one protein having a molecular weight of 50 kDa. The single-stranded DNA in the CAV particles is in the form of a circular minus strand Gelderblom et al., (1989) *Archives Virol.* 109:115–120; Todd et al., (1990) supra; Noteborn et al., (1991) *J. Virol.* 65:3131–3139). In young chickens CAV causes anemia by destruction of erythroblastoid precursor cells and immune deficiency by depletion of thymocytes. Lesions occur in the spleen and liver (Jeurissen et al., (1989) *Thymus* 14:115–123). A recent study has shown that the depletion of thymocytes is caused via apoptosis induced by CAV (Jeurissen et al., (1992) *J. Virol.* 66:7383–7388).

SUMMARY

Compositions and methods are provided for inducing apoptosis in diverse human tumor cells using CAV protein VP3. VP3 ("apoptin") can induce p53-independent apoptosis in human tumor cells. The method involves providing to a host VP3, and optionally one or more of VP1 and VP2, in an amount sufficient to induce apoptosis in a tumor. The invention finds use, for example, in the treatment of cancer cells that do not contain p53 and/or enhanced levels of Bcl-2 or BCR-ABL.

BRIEF DESCRIPTION OF THE DRAWING

FIG. 1 (SEQ ID NOS:3 and 4) gives the DNA sequence and the amino acid sequence of the VP1 protein of Chicken Anemia Virus. The numbering of the CAV DNA sequences is as given in Dutch patent no. 9002008.

FIG. 2 (SEQ ID NOS:5 and 6) gives the DNA sequence and the amino acid sequence of the VP2 protein of Chicken Anemia Virus. The numbering of the CAV DNA sequences is as given in Dutch patent no. 9002008.

FIG. 3 (SEQ ID NOS:7 and 8) gives the DNA sequence and the amino acid sequence of the VP3 protein of Chicken Anemia Virus. The numbering of the CAV DNA sequences is as given in Dutch patent no. 9002008.

(hatched bars), or 5 ug of pCMV-Bcl2 plasmid DNA (dotted bars). At least 3 independent experiments were carried out. Per experiment at least 200 apoptin-positive cells were examined.

Figure 20:
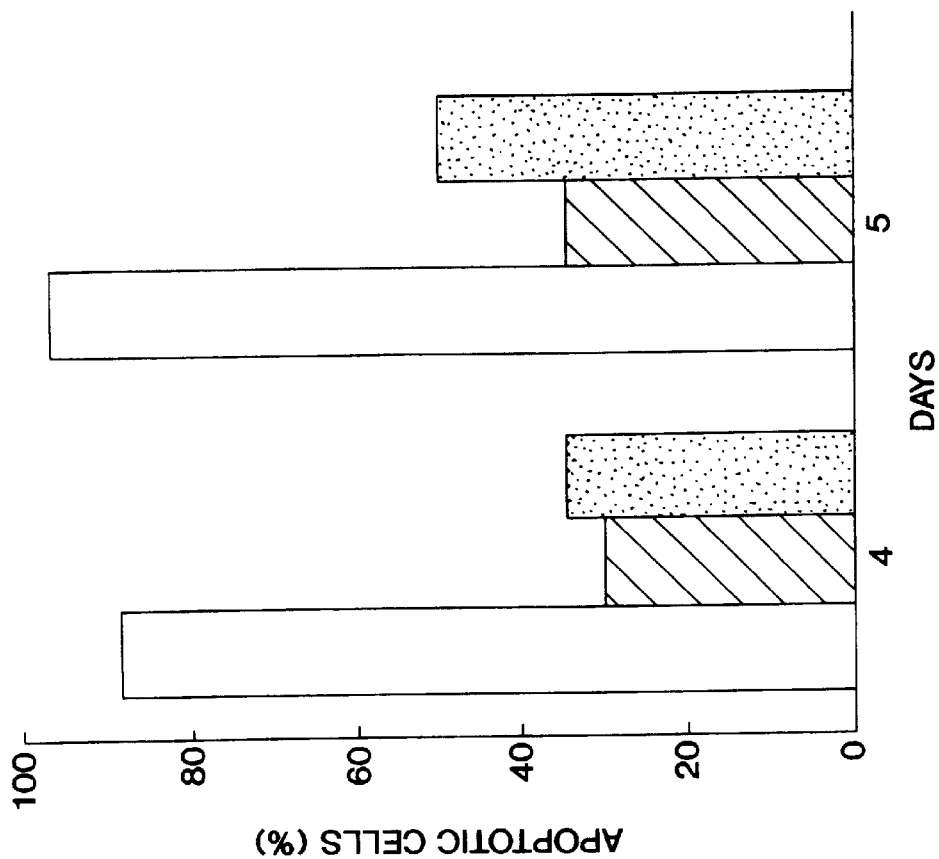

FIG. 20 shows the effect of E1B-21K and Bcl-2 proteins on the induction of apoptosis by p53 in the Hep3B cell line. The cells were co-transfected with 2.5 ug of pCMV-p53 and 5 ug of pCMV-neo-Bam (open bars), 5 ug of pCMV-E1B21 (hatched bars), or 5 ug of pCMV-Bcl2 plasmid DNA (dotted bars). Two independent transfections were carried out. The cells were analyzed 4 or 5 days after transfection. The percentage given is that of p53-positive cells which are apoptotic. Per experiment at least 200 p53-positive cells were examined.

SPECIFIC DESCRIPTION OF THE SPECIAL EMBODIMENTS

The present invention relates to processes for the preparation of recombinant parts of CAV comprising sequences, and processes for the preparation of vaccines are also subjects of the invention and use of the proteins of the CAV in the induction of apoptosis (programmed cell death). In particular, the proteins (polypeptides) can be used in the induction of apoptosis in tumor cells. The proteins according to the invention can also be used in the elimination of other undesired cell populations, such as autoimmune reactive T cells in autoimmune diseases, such a rheumatoid arthritis, lupus, etc. The invention further provides for the induction of cell death by means of gene therapy. Processes for preparing these therapeutics and processes for treatment therewith are also subjects of the invention.

As a way of inducing apoptosis in a tumor, the tumor is supplied with a ligand for a VP3 receptor or VP2 receptor or a VP1 receptor, or a combination of ligands for VP3, VP2 and VP1 receptors. As used herein, the term "VP3 receptor ligand" encompasses compounds that interact with the VP3 receptor such that apoptosis of tumor cells is induced. Examples of such VP3 receptor ligands include various forms of VP3 including truncated forms of VP3 which retain the capacity to bind to VP3 receptors and to effect apoptosis in tumor cells, and other VP3 receptor ligands that demonstrate the capacity to induce apoptosis. Also contemplated are active analogs, fragments and other modifications of the above. Such ligands also include compounds that increase the secretion of endogenous VP3 or similarly active peptides from sites of tissue storage in host animals. By endogenous is intended ligands which are native to the host animal (i.e., indigenous) and also other ligands which are present as a result of infection of the host animal, e.g., by a virus. As used herein, the terms "VP2 receptor ligand" and "VP1 receptor ligand" encompass compounds that bind to VP2 and VP1 receptors, respectively, to effect apoptosis in tumor tissue.

An aspect of the invention is a method for treating a tumor in an individual by administering to the individual a composition including a VP3 receptor ligand and optionally one or more of a VP2 and/or VP1 receptor ligand in an amount sufficient to effect apoptosis in tumor cells. One method of administering the composition is to provide an apoptosis-inducing amount of a VP3 receptor ligand, preferably VP3, to the individual.

Another method of administering the VP3 receptor ligand is by expression of a gene construct transgenically introduced into the tumor and/or its environs. Alternatively, the VP3 receptor ligand is provided by expression of a VP3 receptor ligand gene transgenically introduced into the animal. Preferably, the VP3 receptor ligand is VP3. Similarly, VP2 and/or VP1 receptor ligands can be provided.

In another embodiment, apoptosis is effected by coexpression of (i) a VP3 receptor ligand gene, and (ii) a VP2 and/or VP1 receptor ligand gene that have been stably introduced into the animal. The VP3 receptor ligand is preferably VP3 and the VP3 receptor ligand gene is preferably a VP3 gene.

The nucleic acid construct is generally an expression cassette comprising regulatory regions for control of transcription and/or translation operably linked to nucleic acid encoding a VP3 receptor ligand and/or VP2 or VP1 receptor ligand. The regulatory regions chosen are functional in the intended test animal. This construct includes a nucleic acid sequence coding for the VP3 receptor ligand and an appropriate transcriptional regulatory sequence, which is 5' to and effective to support transcription of a sequence encoding the VP3 receptor ligand. The VP3 receptor ligand preferably is VP3, more preferably CAV VP3. The expression cassette generally is included in a vector, generally a plasmid or it can be a phage which has a transcriptional regulatory sequence providing for the desired transcriptional activity.

Modes of administration include but are not limited to transdermal, intramuscular, intraperitoneal, intravenous, subcutaneous, intranasal, and oral routes. The compounds may be administered by any convenient route, for example, by infusion or bolus injection by absorption through epithelial or mucocutaneous linings (e.g., oral mucosa, rectal and intestinal mucosa, etc.) and may be administered together with other biologically active agents. Administration is preferably systemic.

The present invention also provides pharmaceutical compositions. Such compositions comprise a therapeutically effective amount of a therapeutic, and a pharmaceutically acceptable carrier or excipient. Such a carrier includes but is not limited to saline, buffered saline, dextrose, water, glycerol, ethanol, and combinations thereof. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Various delivery systems are known and can be used to administer a therapeutic of the invention, e.g., encapsulation in liposomes, microparticles, microcapsules and the like.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ameliorate any pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the therapeutic of the invention which will be effective in the treatment of a particular disorder or condition will depend on the nature of the disorder or condition, and can be determined by standard clinical techniques. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

It has been found that the induction of cell death as induced by CAV can essentially be attributed to VP3 and partly to VP2. By deletion of the C terminal 11 amino acids of VP3 the induction of apoptosis by VP3 is strongly reduced. Consequently, the pathogenic activity of CAV can be drastically reduced by introduction of a stop codon into the C terminal region of VP3. The extra stop codon in the coding region for VP3 is introduced into the CAV clone pCAV/EcoRI (Noteborn and De Boer (1990), Dutch Patent No.9002008) which contains the complete CAV genome. The complete CAV mutant genome is cut from the vector and recycled. MDCC-MSB1 cells are transfected with the recycled CAV mutant DNA, and the virus offspring which are less pathogenic are harvested. Chickens are vaccinated with the attenuated CAV mutant viruses. Since the VP2 protein also has an effect on the induction of apoptosis, it is possible to also prepare attenuated CAV which contains a mutation in the coding region for VP2 or VP2 and VP3. The above-mentioned introduction of a stop codon into the coding region for VP2 and/or VP3 can also be used in the production of CAV recombinant living virus vectors.

By means of the antibodies generated with recombinant CAV proteins, CAV proteins can be identified. On the basis of these data, reliable diagnostic tests can be developed. The monoclonal and polyclonal antibodies according to the invention may also be used in other diagnostic assays, such as ELISAs, RIAs, SPIAs, immunofluorescence assays and immunoperoxidase staining, optionally together with one or more CAV proteins or fragments thereof. In principle, all known embodiments of immunological diagnostic tests are possible with all available labels, and depending on the test to be carried out and the conditions under which it must be carried out, a person of ordinary skill in the art will be able to select the most suitable embodiment. Besides, for the purpose of this invention anti-bodies and/or other proteins/polypeptides are also derivatives and/or fragments, as far as they possess the desired activity. In the case of antibodies this means that they must at least be able to recognize the antigen.

CAV induces apoptosis in infected thymocytes. It is possible that a CAV infection of (human) tumors also results in the cell death of the tumor cells. In vitro the CAV protein VP3 is in itself capable of inducing apoptosis in chicken mononuclear tumor cells and in diverse human tumor cells. Expression of the CAV protein can therefore also be used for the induction of cell death in (human) tumors. The VP3 protein can be (transiently) expressed in tumors by means of DNA transfection. Expression of VP3 in (tumor) cells may also be take place by infecting the cells with (retro)viral vectors that contain a coding sequence for VP3. Administration to cells of non-viral components (e.g. liposomes or transferrin-derived vectors) containing VP3 proteins and/or coding sequences for VP3 is a further possibility for the expression/presence of VP3 in (tumor) cells. The above-mentioned uses may also serve for the possible induction of cell death by expression in (tumor) cells of VP2 or VP2 together with VP3.

The CAV proteins VP2 and/or VP3 can be used in treatments for reducing (human) tumor formation. This may take place, e.g., by injecting the proteins according to the invention directly into a solid tumor or coupling the proteins to a ligand having affinity to a tumor associated antiligand. This coupling can be effected both chemically and (in case the ligand is also a protein) via making recombinant a fusion protein. The chemical coupling can be effected directly or via a spacer group. Optionally, an inert carrier molecule may be selected, such as an indifferent serum protein, to which both the ligand and the viral protein are attached, whether or not via a spacer group. Examples of frequently proposed combinations of ligand-antiligand interactions are ligand-receptor pairs, such as EGF/receptor, IL-2/receptor, /T cell receptor, antibody/tumor antigen, etc. Preference is to be given to a ligand-antiligand combination that can be internalized by the cell. When a conjugate is selected, it can be advantageous to apply an intrinsic unstable group as a coupling between the viral protein and the ligand, so that the viral protein in the cell returns in native form. Not in all cases will it be necessary to select an internalizing combination. Tumor cells are metabolically active and will actively or passively take up substances, i.e., also the proteins according to the invention, via phagocytosis and/or pinocytosis. The ligand to which the proteins according to the invention can be coupled in any manner whatsoever need not be a complete ligand. In general, it will be sufficient to use the antiligand binding part. Also derivatives of the ligands in question will be useful as long as they possess the antiligand binding activity. In case the ligand is an antibody, the fact is to be considered that antibodies of another origin than the type to which they are administered will in most cases lead to an immune response. Besides, this also applies to a number of other protein ligands.

It has meanwhile become sufficiently known that antibodies can be manipulated in such a manner that they generate no immune response but still recognize the desired antigen.

It will be briefly explained hereinafter how animal antibodies can be made suitable for human use (humanizing), but it may be clear that also adaptations of another type are possible. In the first place, it is possible to chemically remove the constant part from the antibody to be humanized, so as to prepare FAB, FAB2 or still smaller fragments (Winter et al., (1990) EP patent application 0368684). In general, these fragments will at least be less immunogenic. Such fragments can also be prepared by means of recombinant DNA technology. Besides, it is possible to replace the constant parts of animal antibodies by their human counterparts by means of recombinant DNA technology (Cabilly et al., (1984) EP patent No. 0125023), Boss et al., (1984) EP patent No. 0120694). Besides, it is further possible to inoculate the antigen-binding domains of animal antibodies into antibodies of human origin (Winter et al., (1987) EP patent No. 239400).

Known tumor antigens against which antibodies have been generated are, e.g., CEA (carcino embryonic antigen) and the like.

The invention will be explained in more detail on the basis of the following experimental part. This is only for the purpose of illustration and should not be interpreted as a limitation of the scope of protection.

EXAMPLES

Methods and Materials

Baculovirus, insect cells and chicken T cells

The recombinant baculovirus pAcRP23-lacZ (Bishop, 1992) In: Baculovirus and recombinant protein production processes. (1992). Eds Vlak et al., Editiones Roche, F. Hoffmann-La Roche Ltd., Basel, Switzerland) was obtained from Dr. R. Possee, NERC Institute of Virology, Oxford, England, and the genomic DNA was purified as described by Summers and Smith, (1987) A Manual of Methods for Baculovirus Vectors and Insect Cell Culture Procedures, Texas Agricultural Experiment Station Bulletin No. 1555. *Spodoptera frugiperda* (Sf9) cells were obtained from the American Tissue Culture Collection (no. CRL 1711). Baculovirus stocks were grown in confluent monolayers and suspension cultures in TC 100 medium (Gibco/BRL) containing 10% fetal calf serum as described by Summers and Smith (1987) supra.

The T cell line MDCC-MSB1 transformed with Marek's disease virus (Yuasa, (1983) *National Institute of Animal Health Quarterly* 23:13–20; Yuasa et al., (1983) *National Institute of Animal Health Quarterly* 22:78–81) was grown in RPMI-1680 medium (Gibco/BRL) containing 5–10% fetal calf serum; the cells were used for DNA transection experiments.

Cell Lines

Various human tumor-cell lines with a different p53 status were used for transient DNA transfections. The human osteosarcoma cell lines U2OS and Saos-2 express wild-type p53 and no p53 (Diller et al., (1990) Mal. Cell. Biol. 10:5772–5781, respectively. The human hepatoma cell line Hep3B lacks p53 (Duisieux et al., (1993) Faseb J. 7:1407–1413) and the human kidney rhabdoid tumor cel lines G401 (Garvin et al., (1993) Am. J. Patient 142:375–380) and G401/6.1 express wild-type p53. G401/6.1 cells were derived from G401 cells, by stable transfection of E1B-21kD.

U2OS, Saos-2 and Hep 3B cells were grown in DMEM (Gibco/BRL) containing 10% fetal-calf serum. G401 and G401/6.1 cells were grown in DMEM containing 10% fetal calf serum, 15 ug/ml hypoxanthine and 5 ug/mi thymidine. For culturing G401/6.1 cells, 200 ug/l G418 was added to the medium.

Example 1

Cloning of CAV DNA

All CAV DNA sequences are originally derived from the plasmid DNA Pic-20H/CAV-EcoRI (Noteborn and DeBoer, (1990) Dutch Patent No. 9002008). All cloning steps with plasmid DNA were in principle carried out according to the methods described by Maniatis et al., (1982) (Molecular Cloning: A Laboratory Manual. New York: Cold Spring Harbor Laboratory). The coding sequences of the three CAV proteins VP1, VP2 and VP3 were cloned separately into the baculovirus transfer vector pAcYM1 (Matsuura et al., (1987) *J. Gen. Virol.* 68:1233–1250), which was obtained from Dr. D. H. L. Bishop, NERC Institute of Virology, Oxford, England.

The CAV genome contains three large open reading frames which partially or completely overlap each other. By using start codons in different reading frames the CAV genome codes for three unique proteins. The coding sequences for the CAV proteins were separately (VP1, FIG. 1; VP2, FIG. 2; and VP3, FIG. 3) cloned into the baculovirus transfer vector pAcYM1. (Matsuura et al., (1987) J. General Virology 68:1233–1250), which was obtained from Dr. D. H. L. Bishop, NERC Institute of Virology, Oxford, England. Because the VP3 reading frame completely falls within the VP2 reading frame, VP3, in case of expression of VP2, is always synthesized too, though in a clearly lesser degree. The transfer vector pAcYM1 lacks the coding sequences for polyhedron, the polyhedron promoter inclusively contains the A-residue of the start codon for the polyhedron gene and the 3'-non-coding sequences including the polyadenylation signal. On both sides of the polyhedron sequences are flanking viral sequences. The transfer vector contains prokaryote sequences for multiplication in bacteria (Matsuura et al., (1987) supra).

Figure 4:
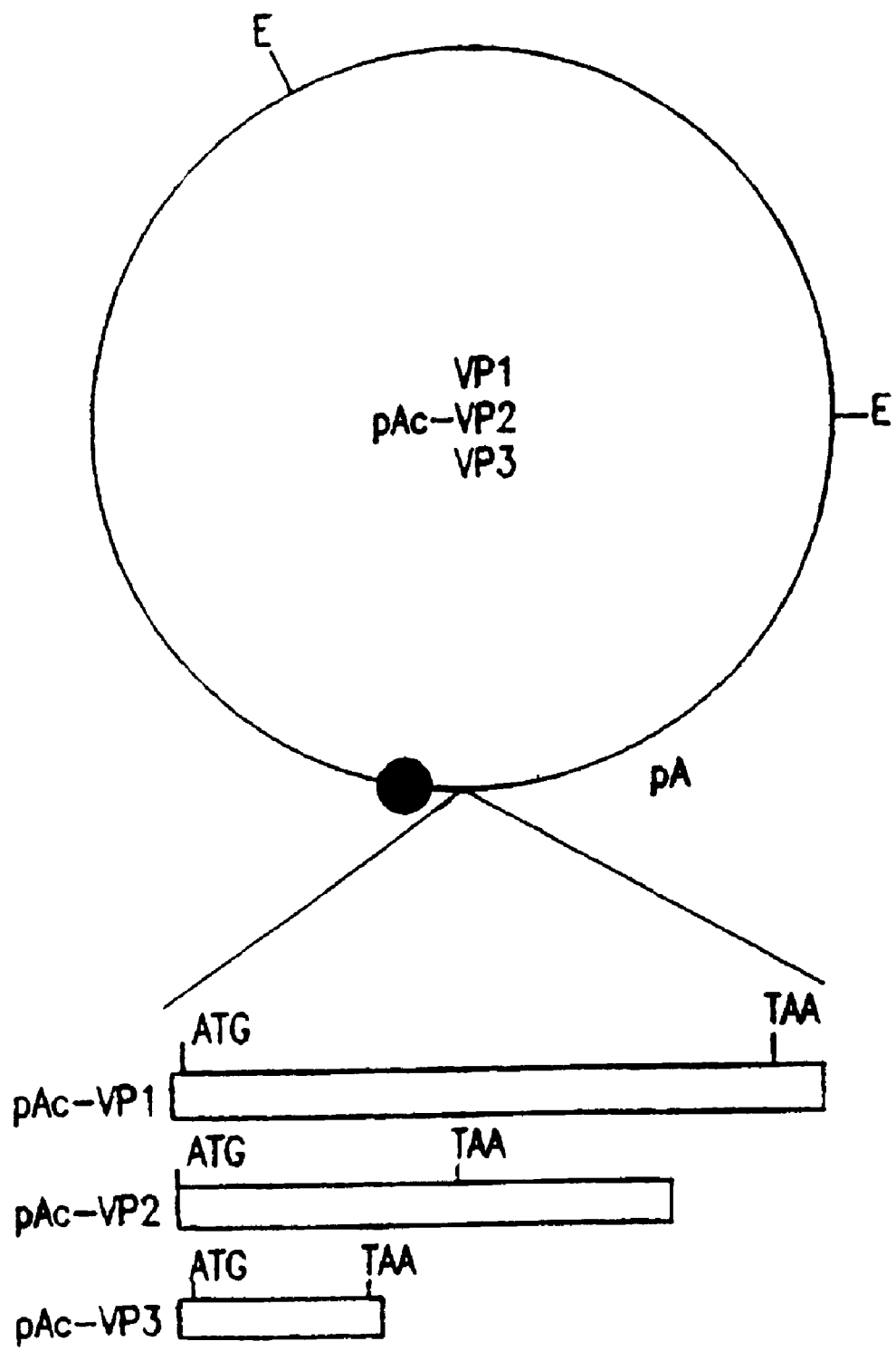
FIG. 4 shows the diagrammatic representation of the 3 CAV recombinant transfer vectors pAc-VP1, pAc-VP2 and pAc-VP3. ●=polyhedrin promoter, ATG=initiation codon, pA=polyadenylation signal, E=EcoRI.

The plasmid pEP-51.6 (Noteborn et al., (1992) Gene[2] 118:267–271) contains CAV DNA sequences of positions 791 to 2319. The CAV DNA insertion contains the complete coding region for the protein VP1 flanked by 62 bp 5'- an 117 bp 3'-non-coding DNA sequences. The plasmid pEP-51.6 was partially cut with HindIII, then completely cut with EcoRI, and the 'sticky ends' were filled by means of Klenow polymerase. A 1.53 kb CAV DNA fragment was isolated. The plasmid pAcYM1 was linearized with BamHI, the sticky ends filled by means of Klenow polymerase and finally treated with calf intestine alkaline phosphatase (CIP). The 1.53 kb CAV DNA fragment was ligated at the linearized pAcYM1 DNA. The orientation of VP1 in pAcYMl DNA was determined by restriction enzyme analysis, and the final construct pAcVP1 is shown in FIG. 4.

To generate a recombinant transfer vector containing VP2-coating sequences, plasmid pEP-24.0, which contains the 1.15 kb BamHI DNA fragment with CAV DNA sequences of positions 354 to 1508 (Noteborn and De Boer, (1990) supra) was used. This CAV DNA fragment contains the coding region for VP2 flanked by 26 bp 5'- and 484 bp 3'-non-coding DNA sequences. 106 bp downstream of the start codon for VP2 the start codon for VP3 is found in another reading frame, and the other coding sequence for VP3. The plasmid pEP-24.0 was treated with BamHI; the 1.15 kb DNA fragment was isolated and ligated into at the BamHI linearized and CIP treated 9.3 kb pAcYM1 plasmid. The final DNA construct pAcVP2 was characterized with restriction enzymes and is shown in FIG. 4.

To construct a transfer vector with sequences coding VP3, plasmid pEP-13.3 was used which contains the 0.46 kb BamHI-EcoRI DNA fragment with CAV DNA sequences of positions 427 to 868 (Noteborn and De Boer, (1990)). The CAV DNA fragment contains the coding region for VP3, 58 bp 5'- and 25 bp 3'-non-coding DNA sequences. Plasmid pEP-13.3 was cut with the restriction enzymes BamHI and EcoRI, and a 0.46 kb BamHI-EcoRI fragment was isolated.

Transfer vector pAcYM1 DNA was linearized with BamHI and treated with CIP, and a 9.3 kb fragment was isolated. The two synthetic DNA oligomers 5'-GATCCAACCCGGGTTG-3' (SEQ ID NO:1) and 5'-AATTCAACCCGGGTTG-3' (SEQ ID NO:2) were hybridized to each other and together form a BamHI-EcoRI DNA linker. The DNA linker was ligated at the 0.46 BamHI-EcoRI, and the 9.3 kb BamHI DNA fragment. The final construct pAc-VP3 was analyzed by restriction enzyme digestions and is shown in FIG. 4.

DNA transformations were carried out in the *E. coli* strain HB101. All plasmids were multiplied in large cultures under agitation, purified on CsCl gradients, and then by filtration over Sephacryl S-500 columns.

DNA Transfection: Construction of Recombinant CAV Baculovirus

DNA of the recombinant baculovirus AcRP23-lacZ was isolated from extracellular baculoviruses according to a method described by Summers and Smith (1987) supra. The lacZ gene contains a unique cutting site for the restriction enzyme Bsu36I. The AcRP23-lacZ was linearized by digestion with Bsu36I. Sf9 cells were transfected with calcium phosphate precipitates of linearized baculovirus ACRP23-lacZ DNA and recombinant transfer vector DNA according to the method of Smith et al. (1983) Mol. Cell Biol. 3:2156–2165; this is an adaptation of the transection protocol of Graham and Van der Eb (1973) Virology 52:456–467 for Sf9 cells. Each of the three recombinant CAV transfer vectors was transfected separately, together with the recombinant baculovirus AcRP23-lacZ DNA, in Sf9 cells. Transfection occurred with "naked" baculovirus DNA and transfer vector DNA.

Figure 5:
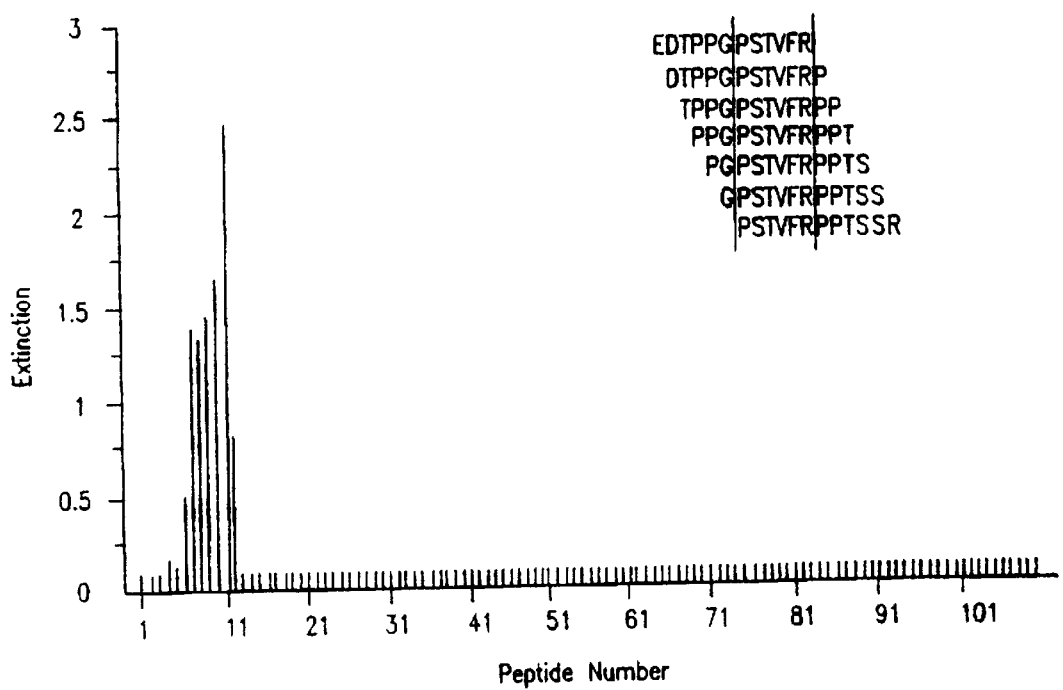
FIG. 5 (SEQ ID NOS:9–15) shows the pepscan analysis of the monoclonal antibody CVI-CAV-85.1 with peptides (12-mers) derived from VP3. The core sequence PSTVFR (SEQ ID NO:30), against which the monoclonal CVI-CAV-85.1 is directed, is at positions 12 to 17 of the VP3 amino acid sequence (Noteborn et al., 1991).
Figure 6:
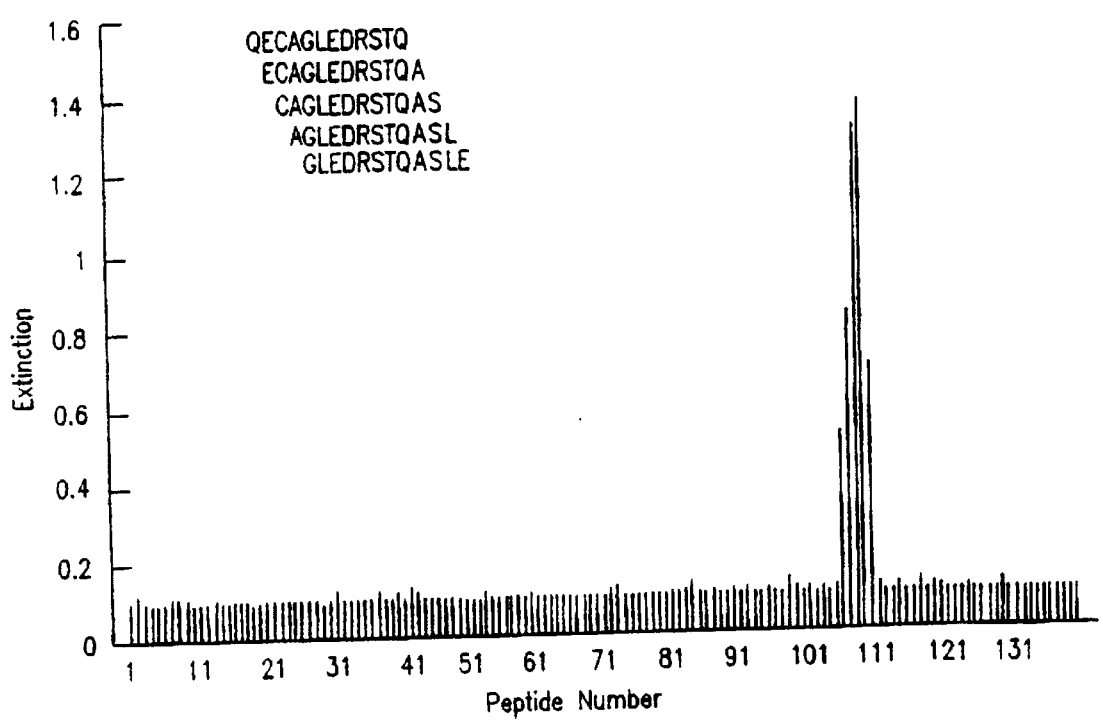
FIG. 6 (SEQ ID NOS:16–20) shows the pepscan analysis of the monoclonal antibody 111.2 with peptides (12-mers) derived from VP2. Monoclonal 111.2 is directed against the epitope GLEDRSTQ (SEQ ID NO:31) which is at positions 109 to 116 of the VP2 amino acid sequence (Noteborn et al., 1991). Only the results obtained with peptides nos. 1 through 140 are shown (extinction of peptides nos. 141 through 206≦0.103).
Figure 7:
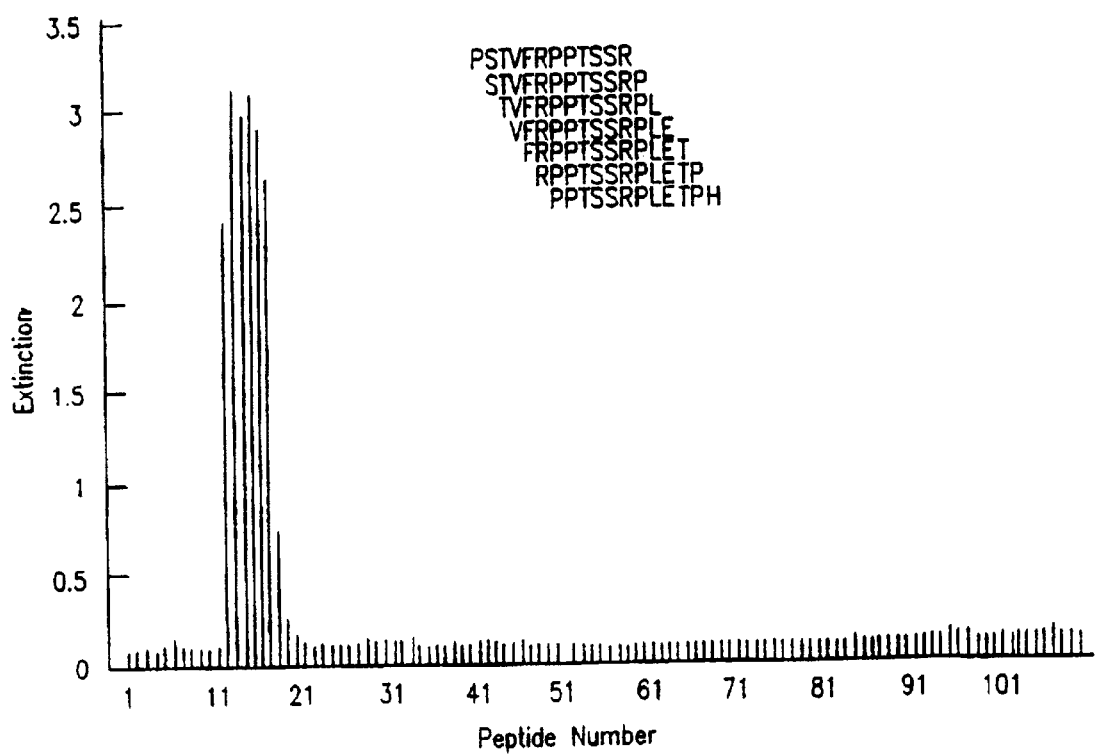
FIG. 7 (SEQ ID NOS:21–27) shows the pepscan analysis of the monoclonal antibody 111.3 with peptides (12-mers) derived from VP3. Monoclonal 111.3 is directed against the epitope PTSSR (SEQ ID NO:32) which is at positions 19 to 23 of the VP3 amino acid sequence (Noteborn et al., (1991) J. Visal 65:3131–3139.

For the transection of the diverse human and chicken cell lines 10 micrograms of pRSV-VP3, pCMV-VP3 pRSV-tr or pRSV-tr DNA were resuspended in 25 microliters of Milli-Q water and mixed with 260 microliters of TBS buffer. 15 microliters of 10 mg/ml DEAE dextran were added to the DNA mixture which was incubated for 30 minutes at room temperature. The cells were centrifuged at 1500 rpm in a table centrifuge. The medium was replaced by 5 ml TBS buffer, and the cells were carefully resuspended. The cells were pelleted, and the TBS buffer was removed. The cell pellet was carefully resuspended in 300 microliters of DEAE dextran/DNA mix and incubated for 30 minutes at room temperature. 0.5 ml 25% DMSO/TBS were added, and the suspension was incubated for 3 minutes at room temperature. 5 ml TBS were added, and the cells were centrifuged at 1500 rpm in a table centrifuge. The supernatant was removed, and 5 ml tissue medium were added.

The cells were resuspended, centrifuged, taken up in 5 ml tissue culture medium and incubated at 37° C.-5% $CO_2$.

Selection of Recombinant CAV Baculovirus

The AcRP23-lacZ baculovirus genome contains, instead of the polyhedron gene, the lacZ gene, under the regulation of the polyhedron promoter. After homologous recombination baculoviruses were obtained which had always incorporated one of the three CAV genes instead of the lacZ gene and thus under regulation of the promoter of the polyhedron gene. The baculoviruses which have correctly incorporated the CAV gene no longer contain the lacZ gene. In the first instance, the recombinant CAV viruses were characterized for the absence of β-galactosidase activity in plaques of baculovirus infected insect cells. The supernatants containing extracellular baculoviruses were analyzed in a plaque essay with neutral red (Brown and Faulkner, (1977) J. Gen. Virol. 36:361–364) and X-gal (Brown et al., (1991) J. Virol. 65:2702–2706). The lacZ-negative plaques were inoculated on a monolayer of Sf9 cells in microliter dishes. Five days after infection the supernatants were harvested and stored at 4° C.

Further the integration of CAV DNA sequences in the baculovirus genome was determined by means of a CAV-specific DNA probe in a hybridization experiment. The cell lysates were analyzed in a dot slot hybridization assay with $^{32}P$ labeled pIc-20H/CAV-EcoRI DNA as a probe.

Expression of the CAV Proteins in Sf9 Cells

The expression of the specific CAV proteins in Sf9 cells infected with recombinant CAV was analyzed by protein labeling with $^{3}H$ leucine and PAA-SDS gel electrophoresis. Monolayers of Sf9 cells were inoculated with supernatants of cell lysates which strongly hybridized with the labeled CAV DNA probe. Two days after infection the cells were labeled with $^{3}H$ leucine. The proteins were separated on 14% polyacrylamide (PAA) SDS gels (Laemmli, (1970) Nature 227:680–685, made visible by means of a fluorography method and tested for the presence of specific recombinant CAV protein and the absence of the β-galactosidase protein.

Synthesis of Crude CAV Protein Preparations

Recombinant CAV baculoviruses which expressed the expected CAV protein in infected Sf9 cells, were dished up according to the method described by Summers and Smith (1983) supra. Monolayers of Sf9 cells were infected with one type of recombinant CAV baculovirus having a multiplicity of infection (moi) of approximately 5 plaque-forming units (pfu) per cell. Co-infections of two or three different CAV recombinant baculoviruses were carried out on Sf9 cell monolayers having a moi of 10 pfu of each recombinant CAV baculovirus per cell. Three days after infection the infected Sf9 cells were harvested. The crude cell lysates were suspended in PBS buffer.

The CAV protein VP1 has a calculated molecular weight of 51.6 kDa (Noteborn and De Boer, (1990) supra). Lysates of insect cells infected with recombinant VP1 baculovirus contain a protein of 52 kDa beside baculoviral and cellular products. The 52 kDa protein was absent in lysates of insect cells infected with the baculovirus AcRP23-lacZ and in non-infected cells. In vitro expression of the coding sequence of VP1 resulted in a protein of 52 kDa (Noteborn and De Boer, (1992) supra). Most probably, VP1 is not glycosylated because VP1 which is synthesized in a rabbit reticulocyte lysate and VP1 synthesized in insect cells have the same molecular weight.

Translation of the gene coding for VP2, but also containing all coding sequences for VP3, produced in an in vitro system specific CAV proteins of 30 and 28 kDa and a minor amount of a 16 kDa protein product. Translation of only the open reading frame coding for VP3 in an in vitro system, however, produced only a protein of 16 kDa. Expression of VP2 by recombinant VP2 baculovirus in infected insect cells produced specific products of approximately 28 kDa and 30 kDa. Sf9 cells infected with a recombinant-lacZ baculovirus do not contain these CAV-specific proteins. The CAV-specific product of 16 kDa could mostly be demonstrated in very small amounts only. These data show that the recombinant VP2 baculovirus strongly expresses the protein VP2 and expresses VP3 in but a minor degree. A possible explanation thereof is that an internal start codon in a gene lying on the baculovirus genome is used very inefficiently.

Recombinant VP3 baculovirus synthesized in infected insect cells a main product of 16 kDa and small amounts of some proteins having molecular weights of approximately 21,000 and 12,000–14,000. In an immunofluorescence assay the CAV-specific monoclonal antibody CVI-CAV-85. 1 reacted specifically with Sf9 cells expressing VP3. This monoclonal antibody precipitated specifically only a protein having a molecular weight of 16,000 from lysates of radioactively labeled Sf9 cells infected with VP3 recombinant baculovirus. In a pepscan analysis (Geysen et al., 1984) the epitope of the monoclonal antibody CVI-CAV-85.1 was localized on the N-terminus of VP3. The pepscan analysis is shown in FIG. 5.

The coding sequence for the CAV protein VP3 and a mutant derived therefrom were cloned into the expression vector PRSV-H2O (Offringa et al., (1990) *Cell:* 527–538). DNA transformations were carried out in the *E. coli* strain HB101. All plasmids were multiplied in large cultures under agitation, purified on CsCl gradients, and then by filtration over Sephacryl S-500 columns.

Example 2

Production and Characterization of Monoclonal Antibodies Specifically Directed Against CAV Proteins The monoclonal antibody CVI-CAV-85.1 was obtained by injecting mice intraperitoneally with CAV injected MDCC-MSB1 cells with incomplete Freund's adjuvant. Finally, spleen cells of the immunized mice were fused with P3X63-Ag8.653 myeloma cells (Noteborn et al., (1991) J. Virol 65:3131–3139). Other monoclonal antibodies directed against CAV antigens were obtained by injecting crude extracts of Sf9 cells infected with the three CAV recombinant baculoviruses into the spleen of four BALB/c mice. The sera of the immunized mice were tested for 7 weeks after immunization for neutralizing antibodies against CAV. The spleen cells of the immunized mice were fused with P3X63-Ag8.653 myeloma cells. Antibodies directed against CAV antigens were tested by different ways: a serum neutralization test; ELISAs based on purified CAV and on crude lysates of Sf9 cells infected with CAV recombinant baculovirus; immunofluorescence tests on CAV infected MDCC-MSB1 or on Sf9 cells infected with CAV recombinant baculovirus; Western blots of crude lysates of Sf9 cells infected with CAV recombinant baculovirus, and immunoperoxidase staining on thymus coupes of CAV infected chickens.

Western blots with CAV antigens produced with the baculovirus expression system showed that the monoclonal antibodies 111.1, 111.2, 111.4, 112.1, 112.2, 120.1 and 120.2 are strongly directed against VP2 and the monoclonal antibodies 111.3 and 120.3 strongly against VP3. The monoclonal antibodies which strongly react with VP2 all show a weak cross reaction with VP3. Conversely, the monoclonal antibodies directed against VP3 show a weak cross reaction with VP2.

The sera of chickens and mice infected with crude Sf9 cell lysates or PBS buffer were diluted 1:2 or 1:4 and then a two-fold dilution series was made. The diluted sera were incubated for 1 hour with $10^4$–$10^5$ $TCID_{50}$ CAV-Cux-1 (Von Bülow et al., (1983) J. Vet. Med. B 30:742–750; Von Bülow, (1985) J. Vet. Medicine B 32:679–693). Approximately one hundred thousand cells of the T cell line MDCC-MSB1 transformed by Marek's disease virus were infected with this mixture of diluted sera and virus. As controls MDCC-MSB1 cells were infected with CAV which was neutralized with a positive CAV antiserum and a negative serum originating from specific pathogen free chickens.

The serum neutralization test showed that none of the monoclonal antibodies obtained had a neutralizing activity against CAV, in spite of the fact that the sera of the immunized mice used for preparing the hybridomas did have a neutralizing activity against CAV.

In a pepscan analysis (Geysen et al., (1984) Proc. Nat'l. Acad. Sci. (USA) 82:1978–1982) the epitope of the monoclonal antibody 111.2 was localized in the middle of VP2 (FIG. 6). The monoclonal antibody 111.3 was found to be directed against an epitope at the N terminal end of VP3 (FIG. 7), namely beside the VP3 epitope recognized by the monoclonal antibodies CVI-CAV-85. 1 (FIG. 5).

Two types of CAV-specific monoclonal antibodies are described above. One type is directed against VP2, while the other is directed against VP3. Neither of these types of monoclonal antibodies reveal a CAV-specific neutralizing activity. Even more important was that none of these monoclonal antibodies was directed against VP1. We assumed that a neutralizing monoclonal antibody might be directed against VP1, for the capsids contain mainly VP1 (Todd et al., (1990) G. Gen Virol. 71:819–823). Below, we describe the production of neutralizing antibodies against CAV.

For the production of neutralizing monoclonal antibodies against CAV, mice were injected with purified CAV particles. The supernatant of a 1 liter culture of CAV-infected MDCC-MSB1 cells was concentrated forty fold by means of a MILLITAN 300-kDa filter (Millipore, USA). The supernatant was dialyzed against 10 mM Tris(ph 8.7)-1 mM EDTA (TE) buffer. Subsequently, sodium dodecyl sulphate (SDS) (0.5% final concentration) was added to the CAV-capsid suspension and incubated for 30 minutes at 37° C. Finally, the CAV capsids were pelleted on a 30% sucrose cushion. The pellet containing the CAV capsids was resuspended in 1 ml TE buffer. Mice were twice injected with 100 ul CAV-capsid suspension.

As a first screening for (neutralizing) monoclonal antibodies against CAV, microtitre wells were coated with recombinant-VP1/VP2-baculovirus infected insect cells, which co-synthesized both VP1 and VP2. CAV-specific antisera with a high neutralizing titer reacted at a dilution of 1:1000 specifically with the recombinant VP1 and/or VP2 products (see below). Several different hybridoma cell lines producing monoclonal antibodies, which specifically reacted with recombinant VP1/VP2 products, were obtained.

A CAV-specific serum neutralization test, carried out as described above, showed that three of these monoclonal antibodies obtained, had a neutralizing activity against CAV. These three CAV-specific neutralizing monoclonal antibodies were called 132.1; 132.2 and 132.3. Immunofluorescence showed that the three neutralizing monoclonal antibodies 132.1, 132.2 and 132.3 recognize specific structures in CAV-infected MDCC-MSB1 cells. None of these monoclonal antibodies reacted with uninfected MDCC-MSB1 cells.

Electron-microscopic analysis was carried out with purified CAV particles incubated with neutralizing antibodies against CAV (132.1) or with monoclonal antibodies 111.1 (against VP2) or 111.3 (against VP3). The various monoclonal antibodies were detected by immunogold labeling. Only the neutralizing monoclonal antibodies 132.1 were found to bind to CAV particles. Binding of the monoclonal antibody 132.1 to a CAV particle resulted in its lysis. Furthermore, CAV capsids, which were lysed due to incubation with the neutralizing monoclonal antibody 132.1, showed no binding with monoclonal antibodies directed against VP2 or VP3.

These results reveal the mechanism by which the neutralizing monoclonal antibodies act: they cause the lysis of the virus capsids, by doing so causing non-infectious particles. Furthermore, these data suggest that purified CAV particles contain (almost) only VP1.

Pepscan analysis (Gheysen et al., (1984) Proc. Nat'l Acad Sci. (USA) (82:178–182)) revealed that none of the three neutralizing monoclonal antibodies reacted significantly with one of the 12-mers derived from VP1 or VP2. For the sake of brevity only the data obtained with monoclonal antibody 132.1 are shown for VP1 in FIG. 14, and for VP2 in FIG. 15. These results indicate that the neutralizing monoclonal antibodies are directed against a conformational epitope. These data were confirmed by the following experiments. Purified CAV particles, dotted on a nylon filter under native conditions, still could react with the neutralizing monoclonal antibody 132.1. However, after boiling in the presence of SDS, the CAV capsid proteins did not bind to monoclonal antibody 132.1.

Immunoprecipitation experiments, carried under native conditions, as described by Noteborn et al., In: Virus Diseases of Poultry-New and Evolving Pathogens, (1994) 195–212, with partially purified CAV particles and monoclonal antibody 132.1, 132.2 or 132.3 showed that a protein of about 50 kDa was precipitated by these monoclonal antibodies. These results indicate that the neutralizing monoclonal antibodies are directed against VP1.

Example 3

Expression of VP3 in Chicken Cells Induces Apoptosis

Figures 8A, 8B:
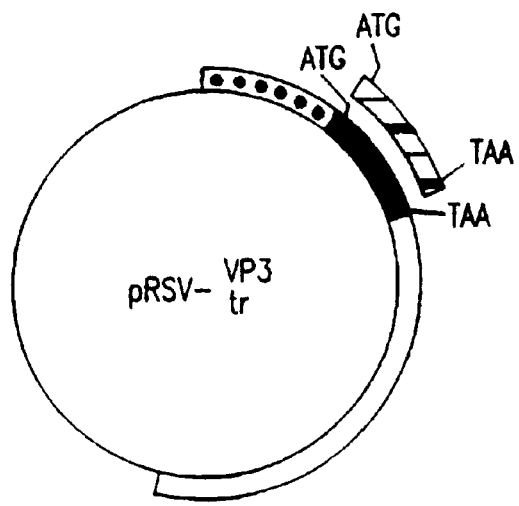
FIG. 8, Panel A shows the diagrammatic representation of the 2 expression vectors pRSV-VP3 and pRSV-tr. ■=VP3, ▨=VP3tr, ▣=RSV LTR, □=SV40. Panel B (SEQ ID NO:7) shows the amino acid sequence of the CAV protein VP3. The proline residues are printed in italics and the basic amino acids in heavy type. The 11 C terminal amino acids, the codons of which are deleted in the expression vector, are underlined.

Jeurissen et al. have shown that CAV causes apoptosis in infected thymocytes. We have studied whether one of the CAV proteins, in particular VP3, is capable of independently inducing apoptosis in chicken T cells. The coding sequences for VP3 were cloned into the expression vector pRSV-20H. The 0.46 kb BamHI-EcoRI fragment with CAV DNA sequences of positions 427–86B (Noteborn et al., (1991) *J. Virol.* 65:3131–3139) were isolated from plasmid pEP-13.3. The CAV DNA fragment contains the coding sequences for VP3, and moreover 58 bp 5' and 25 bp 3'-flanking sequences. The vector pRSV-H20 was linearized with BglII, treated with calf intestine alkaline phosphatase (CIP), and a 4.3 kb fragment was isolated. Two synthetic DNA oligomers 5'-GATCCAACCCGGGTTG-3' (SEQ ID NO:1) and 5'-AATTCAACCCGGGTTG-3' (SEQ ID NO:2) were hybridized and thus formed a double stranded BamHI-EcoRI linker. The BamHI-EcoRI DNA linker and the 0.46 kb BamHI-EcoRI DNA fragment were ligated at the 4.3 kb BglII DNA fragment. The final construct pRSV-VP3 contained the coding region for VP3 under regulation of the Rous sarcoma virus promoter and was controlled by restriction enzyme analysis (FIG. 8a; Noteborn et al., (1993) In: *Vaccines '93*. CSHL Press, Cold Spring Harbor, USA pp. 299–304).

Figure 9:
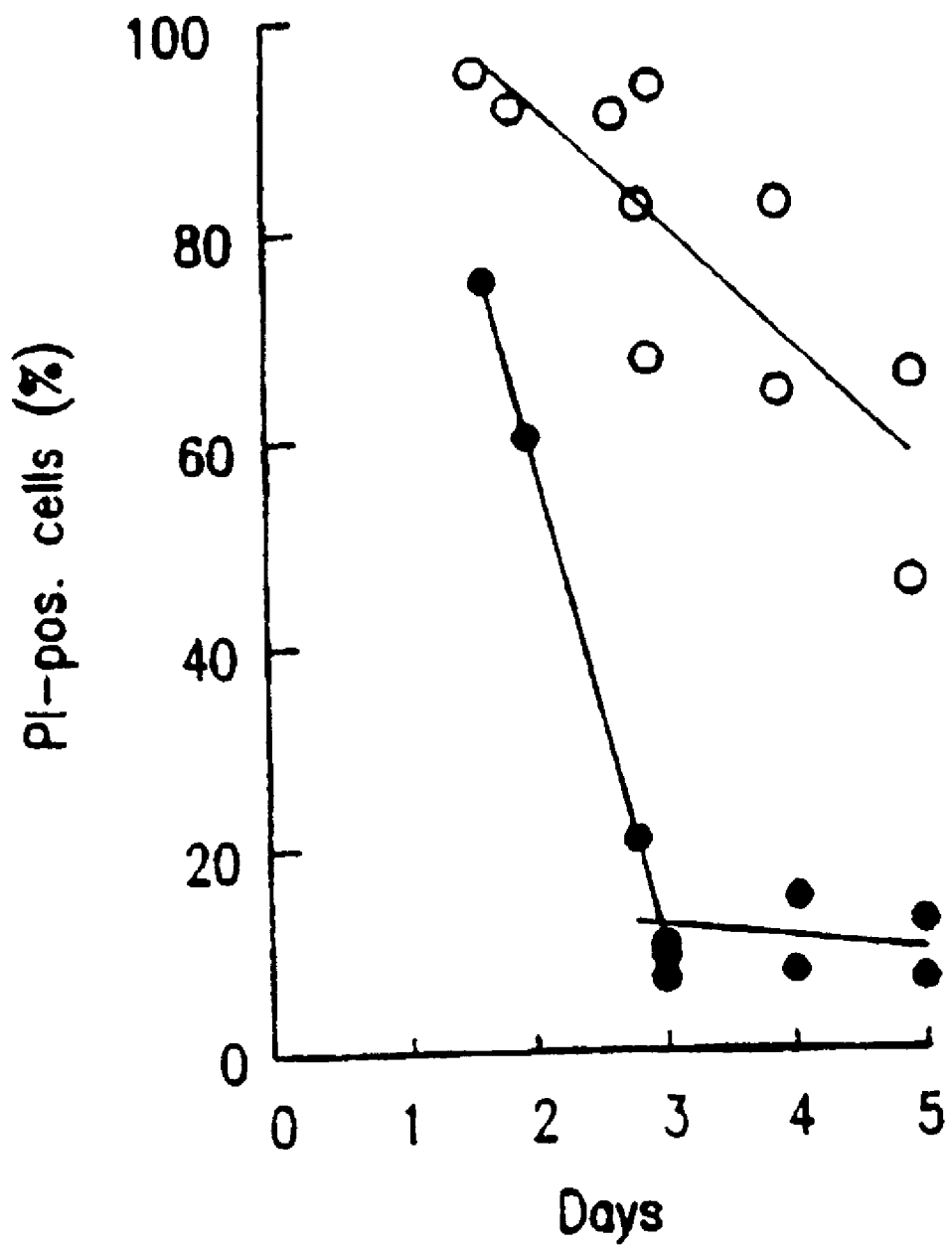
FIG. 9 shows the kinetics of the apoptotic effect of VP3 or truncated VP3. MDCC-MSB1 cells were transfected with plasmid pRSV-VP3 (◎) or pRSV-tr (○), fixed and stained with the monoclonal antibody CVI-CAV-85. 1 at different times after transfection. The percentages of the immunofluorescent cells with nuclei which normally stain with propidium iodide are given. Per experiment at least 100 cells were counted which had expressed VP3 or truncated VP3.

MDCC-MSB1 cells were transfected with DNA of pRSV-VP3 by means of the DEAE dextran method. Forty-two hours after transfection the cells were fixed and analyzed for VP3 expression by staining with monoclonal CVI-CAV-85.1. The cells were also stained with propidium iodide which very strongly stains DNA of intact nuclei but weakly stains DNA of apoptotic nuclei (Telford et al., (1992) *Cytometry* 13:137–143). More than 90% of the transfected cells contained a fine-granular distribution of VP3 in the nucleus which was stained by propidium iodide. Two days after infection 40% of the cells expressing VP3 were found to contain nuclei which were weakly stained with propidium iodide, and VP3 was present as aggregates. Three days and later after infection more than 90% of the VP3-containing cells were found to contain VP3 aggregates and DNA which very weakly stained with propidium iodide (FIG. 9). Three days after transfection the DNA of the VP3 transfected cells showed the oligonucleosomal ladder pattern characteristic of apoptosis.

The VP3 distribution observed in transfected cells fully corresponds with that in CAV-infected MDCC-MSB1 cells. Early after infection (after 1–1.5 day) VP3 is fine-granularly distributed in the nucleus: the cellular DNA is still intact at this stage. Late in infection (after approximately three days) VP3 forms aggregates in the nucleus. The DNA of the CAV-infected cells is fragmented. Our conclusion is that VP3 in itself is capable of inducing the CAV-specific apoptosis in MDCC-MSB1 cells. Expression of pRSV-VP3 DNA coding for VP3 in the monocyte cell line LSCC-HD11 also led to apoptosis in these cells.

Expression of the VP2 protein in MDCC-MSB1 cells also leads to damage to the cellular DNA. Three days after infection of MDCC-MSB1 cells with DNA coding for VP2, in 20% and after 5 days, in approximately half of the transfected cells the nuclei are weakly stained with propidium iodide. Therefore, also VP2, though in a lesser degree than VP3, seems involved in the induction of the CAV-specific cell death.

Example 4

The Effect of Truncated VP3 on the Induction of Apoptosis in MDCC-MSB1 Cells

VP3 is a protein of 121 amino acids in length, contains two proline-rich pieces, a hydrophobic region and two strongly positively-charged portions (FIG. 8b) (SEQ ID NO:7). The positively charged regions are possibly nucleus localization signs and/or DNA-binding domains. We have studied whether the basic C terminal end of VP3 is involved in the apoptotic activity of VP3. To this end, a truncated VP3 production was made by deletion of 11 codons at the C terminus of the VP3-coding sequences. Plasmid pEP-VP3 was cut with the restriction enzymes BamHI and HindIII, and the 0.38 kb BamHI-HindIII DNA was isolated. Two synthetic DNA oligomers, 5'-AGCTTGATTACCACTACTCCCTGAG-3' (SEQ ID NO:28) and 5'-TCGACTCAGGGAGTAGTGGTAATCA-3' (SEQ ID NO:29, were hydridized and thus formed together the double-stranded HindIII-SalI DNA linker. Plasmid pRSV-H20 was cut with BglII and SalI, treated with alkaline phosphatase, and a 4.3 kb DNA fragment was isolated. The HindIII-SalI DNA linker and the 0.38 kb BamHI-HindIII fragment were ligated in the 4.3 kb BglII-SalI fragment. The final construct pRSV-tr containing the coding sequences for the truncated VP3 protein under the regulation of the RSV promoter (FIG. 8a) was analyzed by means of restriction enzyme and sequence analysis. Also see Zhuang et al. (1994) *Cancer Research* 486–489.

MDCC-MSB1 cells were transiently transfected with pRSV-tr DNA and, at different moments after transfection, stained with monoclonal CVI-CAV-85. 1 and propidium iodide. Immunofluorescence showed that 42 hours after transfection most of the cells expressing truncated VP3 contained fine-granular VP3 in their nuclei. The cellular DNA was strongly stained with propidium iodide. Three days after transfection still 80% of the cells expressing truncated VP3 had nuclei which strongly stained with propidium iodide (FIG. 9). DNA isolated from MDCC-MSB1 cells on 3 days after transfection with pRSV-tr was found to be much less degraded than DNA isolated from pRSV-VP3-transfected MDCC-MSB1 cells. The fraction of the propidium iodide positive nuclei of cells expressing truncated VP3 slowly declined to approximately 50% on 5 days after transfection. Most of the cells containing truncated VP3 and weakly stained by propidium iodide had a granular VP3 distribution. Only a single cell contained VP3 aggregates.

The expression of truncated VP3 in MDCC-MSB1 cells apparently induced cell death much less efficiently than expression of wild type VP3. It is also remarkable that the VP3 mutant can form much fewer aggregates than wild type VP3.

Example 5

Expression of VP3 in Human Tumor Cells Induces Apoptosis

Figure 10:
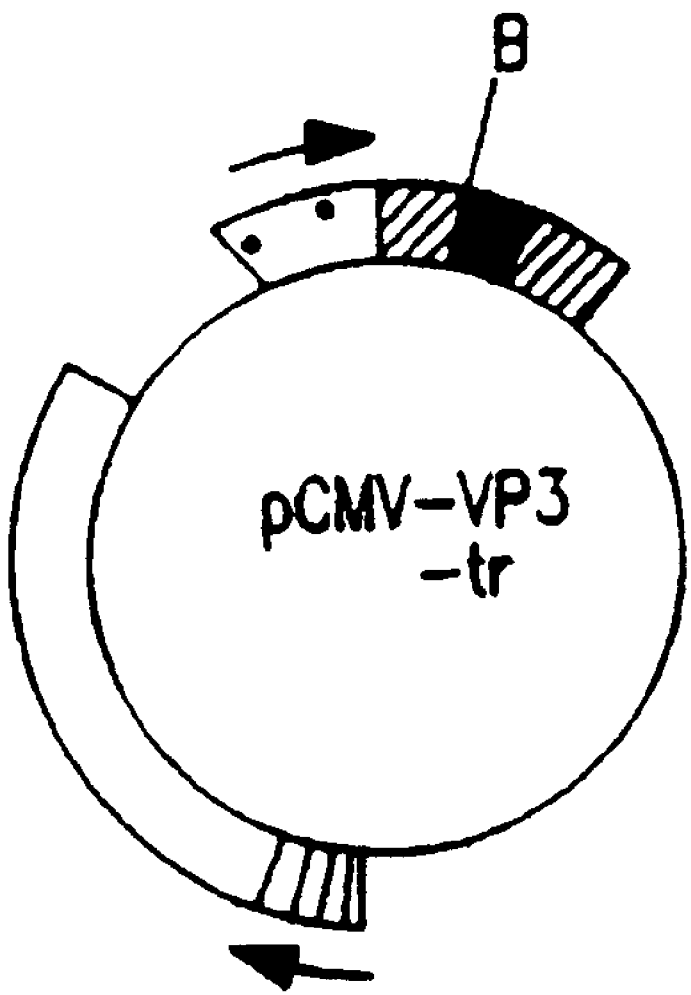
FIG. 10 shows the diagrammatic representation of the expression vectors pCMV-VP3 and pCMV-tr ▣=CMV promoter, ▨=rabbit B-globin, □=neomycin resistance, ■=VP3 or truncated VP3, ▥=RSV promoter, __=pBR322 sequences, B=BamHI cloning site.

For the expression of VP3 in human cells the expression vectors pRSV-VP3 (FIG. 8a) and pCMV-VP3 were used. The coding sequences for VP3 were cloned into the expression vector pCMV-neo containing the strong promoter of the cytomegalovirus (CMV) immediate early gene (Boshart et al., (1985)). The 0.46 BamHI fragment with CAV DNA sequences of positions 427–868 (Noteborn et al., (1991) *J. Virol.* 65:3131–3139) were isolated from plasmid pAc-VP3 (FIG. 4). The vector pCMV-neo was linearized with BamHI, treated with CIP, and a 7.5 kb fragment was isolated. The 0.46 BamHI DNA fragment was ligated at the 7.5 BamHI DNA fragment. The right orientation of the VP3-coding sequence with respect to the CMV promoter in the final construct pCMV-VP3 was determined by means of restriction enzyme analysis (FIG. 10).

For the expression of truncated VP3 in human cells the 0.46 kb XhoI-SalI fragment of plasmid pRSV-tr coding for truncated VP3 (FIG. 8a) was provided with blunt ends by treatment with Klenow polymerase and isolated. The vector pCMV-neo was linearized with BamHI, provided with blunt ends and dephosphorylated by treatment with CIP. The 0.46 kb blunt end DNA fragment was ligated at the 7.5 blunt end DNA fragment. The construct pCMV-tr contains the coding sequences for truncated VP3 under regulation of the CMV promoter (FIG. 10).

Figure 11A:
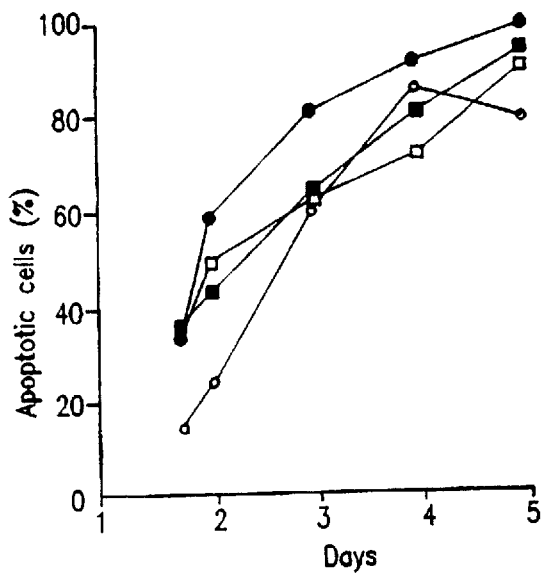
FIGS. 11a and b show the kinetics of the apoptotic effect of VP3 on human hematopoietic (tumor) cells. The cell line KG1 was transfected with plasmid pRSV-VP3, and the cell lines DOHH-2, K562 and Jobo-0 were transfected with plasmid pCMV-VP3. The percentages of the VP3-positive cells with nuclei that weakly stain with propidium iodide, apoptotic cells, are given. Per experiment at least 200 cells were counted. For FIG. 11a: —○—=KG1, —●—=DOHH-2, —□—=K562, —■—=Jobo-O. For FIG. 11b: —○—=K562*pCMV-VP3, —●—=K562*pCMV-trVP 3.
Figure 11B:
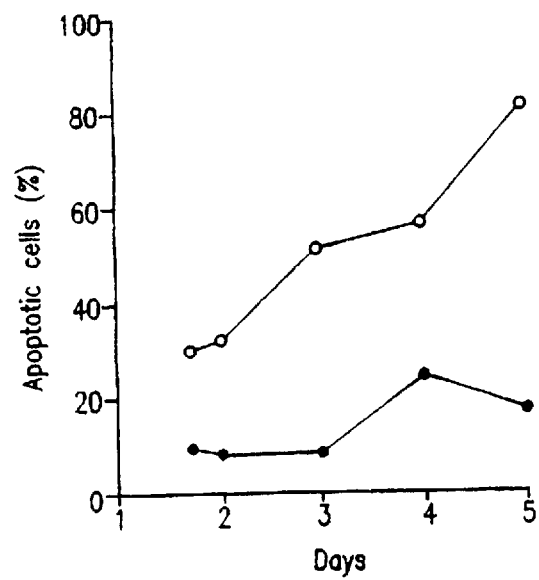

In the first instance, VP3 was expressed in the 3 human hematopoietic tumor cells lines KG-1, DOHH-2 and K562, and in an immortalized cell line, Jobo-0. The cell lines KG-1 and K562 have been derived from different patients with hyman myeloid leukemia and DOHH-2 from a patent with a follicular B-lymphoma. Jobo-0 cells were immortalized with the Epstein Barr Virus. The four human cell lines were transfected with DNA of pRSV-VP3 (KG-1) or with DNA of pCMV-VP3 (DOHH-2, K562 and Jobo-1). The cells were fixed and analyzed for VP3 expression by staining with monoclonal CVI-CAV-85. 1 and induction of apoptosis by staining with propidium iodide. Early after transfection VP3 positive cells were observed with a fine-granular distribution of VP3 in the nucleus which was stained with propidium iodide and VP3 positive cells with nuclei containing VP3 aggregates with nuclei that did not stain with propidium iodide. The percentage of VP3 positive cells with nuclei that did not stain with propidium iodide and contained VP3 aggregates was found for the four different hematopoietic cell lines to range between 75 and 95% 5 days after transfection (FIG. 11a). Then K562 cells were transfected with DNA of the plasmid pCMV-tr which expresses C terminal truncated VP3. Expression of truncated VP3 in K562 cells induced the cell death much less efficient than wild type VP3. Our conclusion is that expression of VP3 in human hematopoietic tumor cells leads to specific induction of apoptosis. Expression of VP3 in the human breast tumor cell line MCF-7 also resulted in the induction of apoptosis.

Figure 12A:
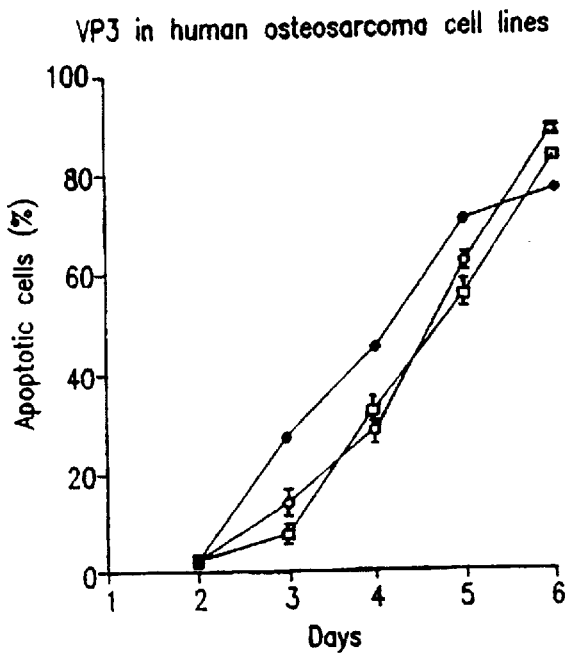
FIGS. 12a and b show the kinetics of the apoptotic effect of VP3 on human osteosarcoma cell lines. Cells of the cell lines Saos-2, Saos-2/Ala143 and U2-OS were transfected with plasmid pCMV-VP3. The percentages of the VP3-positive cells with nuclei that weakly stain with propidium iodide, apoptotic cells, are given. Per experiment at least 500 cells were counted. For FIG. 12a: —□—=Saos-2/Ala143, mutant p53, —○—=Saos-2, p53-, —●—=U2OS, p53+. For FIG. 12b: —○—=Saos-2*pCMV-VP3, —●—=Saos-2*pCMV-trVP3.
Figure 12B:
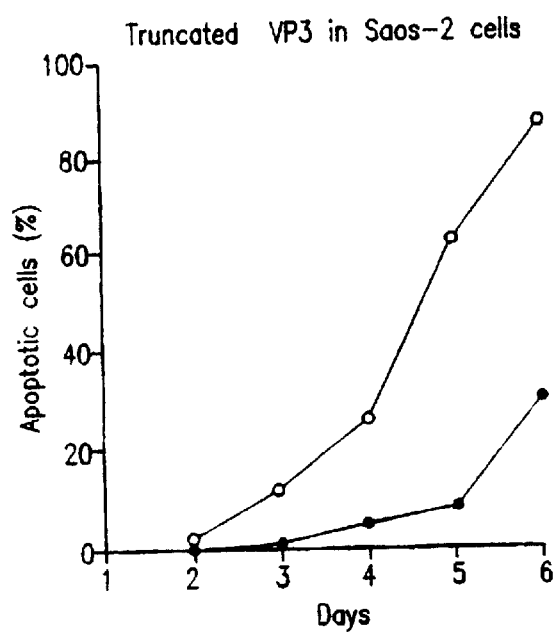

Tumors and tumor cell lines that do not contain function p53 generally are less/not susceptible to induction of cell death by chemotherapeutics and radiation treatment. The tumor suppressor gene p53 acts as intermediary in the induction of apoptosis by specific anti-tumor agents. We have examined whether VP3 is capable of inducing apoptosis in human cells that do not possess p53 or possess mutated p53, VP3 was expressed in human osteosarcoma cells by means of DEAE-dextran transfection with plasmid pCMV-VP3. The osteosarcoma-derived Saos-2 cells cannot synthesize p53, and Saos-2/ala143 cells express mutated and thus non-functional p53. As a positive control the U2-OS cell line containing wild type p53 was used. The results given in FIG. 12a show that VP3 can induce apoptosis in a comparable degree in cells that are p53$^-$ (Saos-2 and Saos-2/Ala143) or p53$^+$ (U2-OS). Six days after transfection most of the VP3 positive cells are apoptotic. Expression of truncated VP3 induced much less efficient apoptosis in Saos-2 cells (FIG. 12b). Our conclusion is that VP3 can specifically induce apoptosis in human tumor cells containing or not containing the tumor suppressor gene p53.

Example 6

Effect of AdsE1B Protein on Apoptin-Induced Apoptosis in P53 and P53+ Human Osteosarcoma Cells Expression Vectors All expression vectors are based on plasmid pCMV-neo-Bam containing the human cytomegalovirus (CMV) promoter (Baker et al., (1990) (Science J. 245:912–915). The CAV sequences originated from plasmid pCAV/E as described by Noteborn et al. (1991) J. Virol, 65:3131–3139. The plasmid pCMV-VP3 encodes apoptin, pCMV-E1B55 (Van den Heuvel (1993) J. Viral 67:5226–5234) specifies the Ad5 E1B-55KDa and pCMV-p53 (Baker et al., (1990) supra) the wild-type human p53. The construction of the expression vector pCMV-E1B21 encoding Ad5 E1B-21kD is as follows: the 1.1-kb Eco-N1-Hind111 fragment derived from plasmid p5x5 (Jochemsen et al., (1990) EMBO J. 6:3399–3405) containing the entire E1B-21kD coding region, was cloned in the BamHl-site of pCMV-neo-Bam.

To express human Bcl-2 in human tumor-cell lines, the expression vector pCMV-Bcl2 was constructed. Plasmid pBK-KS-H-Bcl2 (provided by S. Korsmeyer, The Johns Hopkins University, Baltimore) was digested with dasEcoR1 , treated with Kienow polymerase to create blunt ends and the 1.9-kb DNA fragment containing the human Bcl-2 coding sequences (Seto et al., (1988) EMBO J, 7:123–13) was isolated and ligated into BAMH1-blunt-ended plasmid pCMV-neo-Bam. The final construct pCMV-Bcl2 was analyzed by restriction-enzyme digestions to confirm that the coding sequences for Bcl-2 were correctly oriented with regard to the CMV promoter.

DNA Transfection

Plasmid DNA was purified by centrifugation in a CsCl gradient and by column chromatography in Sephacryl S500 (Pharmacia). One day before transfection, the cells were passed at 30–40% confluency in 5-cm (for indirect immunofluorescent assay) or 9-cm (for Western blotting and DNA-fragmentation analysis) tissue-culture dishes. Cells were transfected with plasmid DNA by calcium-phosphate precipitation as described by Graham and Van der Eb (1973) Viral. 52:456–467).

Indirect Immunofluorescence Assay

Cells grown on coverslips were fixed with 80% acetone and used for single or double immunofluorescence labeling as described by Van den Heuvel et al., (1990) *EMBO J.* 9:2621–2629). To analyze the expression and/or cellular location of apoptin in transfected cells the mouse monoclonal (MAb) CV1-CAV-85.1 (85.1;) was used and for the expression of wild-type p53 the mouse MAb PAb 122 (Gurney et al., (1980) J. Viral, 34:752–763). The rat MAbs 9C10 and 1 G 11 (Zantema et al., (1985) Virol 142:44–58) were incubated with transfected cells to detect E1B-55kD and E1B-21kD proteins, respectively. The mouse kMAb Bcl-2(100) (Santa Cruz Biotechnology, Inc.) was used to examine the expression of the human Bcl-2 protein. Fluorescein isothiocyanate labeled goat anti-mouse (GAM-FITC) or tetramethylrhodamine-isothiocyanate labeled goat anti-rat (GAR-TRITC) antibodies (Jackson Immunoresearch Laboratories, Inc. West Grove, Pa.) were used as second antibodies. Nuclear DNA was stained by propidium iodide (P1) or 2,4-diamidino-2-phenylindole (DAP1).

DNA Fragmentation Analysis

Five days after transfection, cells were harvested and incubated at 37° C. for 1 h in 400 ul lysis buffer (10 mM Tris at pH 8.0, 1 mM EDTA, 0.2% SDS, 0.1M NaCl, 0.5 mg/ml of proteinase K). Cellular DNA was extracted with phenol/chloroform/isoamylalcohol (ratio 25:24:1), ethanol-precipitated, subsequently resuspended in 300 ul TE buffer (10 mM Tris-HCl, pH 7.5, 1 mM EDTA) and rotated at 4° C. overnight. From each sample, 1 ug DNA was fractionated on a 2% agarose gel by electrophoresis at 40 voltage for 6 h. The DNA was transferred onto Hybond-N+ nylon membranes (Amersham) and hybridized to randomly primed$^{32}$P labeled chromosomal DNA, which had been extracted from non-transfected Saos-2 cells.

Western Blotting

Two days after transfection, cells were harvested in SDS-PAGE sample buffer (62.5 mM Tris-HCl (pH 6.8), 10% glycerol, 2% SDS, 5% 2-mercapto-ethanol and 0.05% bromphenol blue). Proteins were separated on 15% SDS-polyacrylamide gels, electroblotted onto Immobilon-P membranes (Millipore) and detected by ECL according to the manufacturer's specifications (Amersham).

Effect of the Ad5 E1B Proteins

Figure 13A:
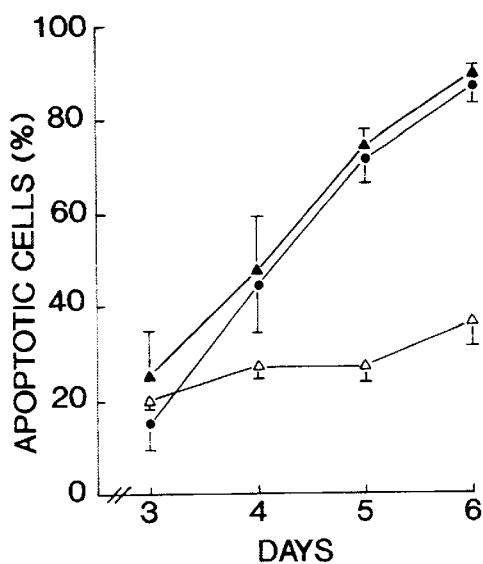
FIG. 13 shows the effect of expression of Ad5 E1B proteins on the apoptotic activity of apoptin in p53+ U2OS and p53- Saos-2 cells. The percentage of apoptin-positive cells which are apoptotic was determined at several time points after co-transfection of Saos-2 (panel A) or U2OS (panel B) cells with 2.5 ug pCMV-VP3 DNA and 5 ug pCMV-neo-Bam DNA (closed circle), 5 ug pCMV-E1B55 DNA (closed triangle), or 5 ug pCMV-E1B21 DNA (open triangle). Panel C. Dose-dependent inhibitory effect of Ad5 E1B-21kD on apoptin-induced apoptosis. Saos-2 cells were co-transfected with 7.2 ug pCMV-VP3 and 1, 0.5 or 0.1 ug pCMV-neo-Bam DNA (open bar) or pCMV-E1B21 DNA (closed bar). The cells were harvested 6 days after transfection. Per time point at least three independent experiments were carried out. Per experiment at least 200 apoptin-positive cells were examined.
Figure 13B:
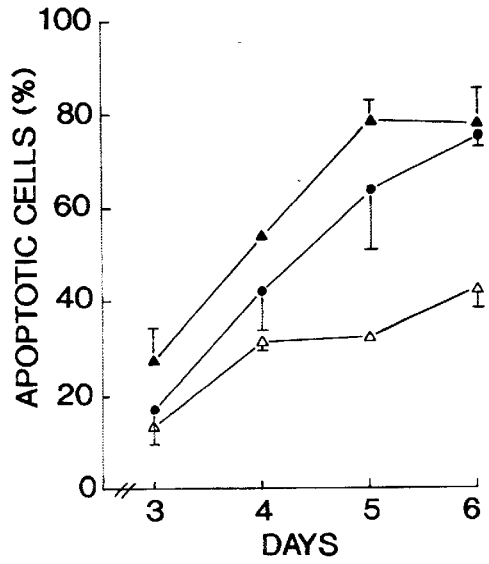
Figure 13C:
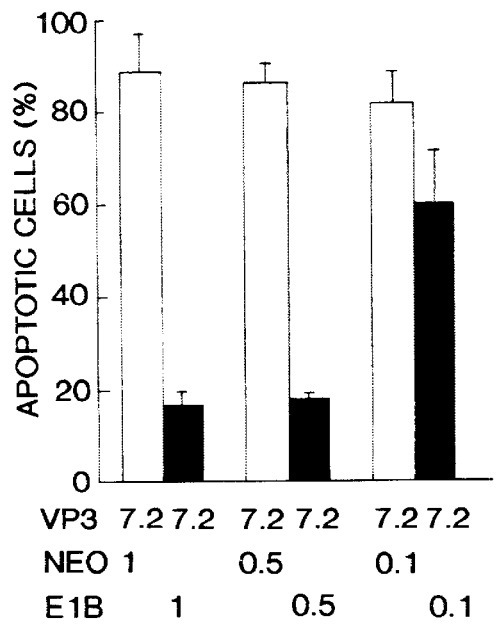

To examine whether E1B-55kD and E1B-21kD can influence the apoptin-induced p53-independent apoptotic pathway, the human osteosarcoma cell lines U2OS (wild-type p53) and Saos-2 (p53-negative) were transiently co-transfected with plasmid DNA pCMV-VP3 and pCMV-neo-Bam (negative control), pCMV-E1B55, or pCMV-E1B21. At various time points after transfection, the cells were screened for expression of apoptin and the E1B proteins 21kD or 55kD by indirect immunofluorescence. In general, 1–5% of the transfected cells produced the exogenous proteins. Apoptosis was determined by staining with P1 or DAP1, which are known to stain intact nuclei strongly, but apoptotic nuclei irregularly and weakly Telford et al., (1992) (Cytometry 13:137–143 and Zhuang et al., (1995) Cancer Research 55:486–489). The percentage of apoptin-expressing Saos-2 and U2OS cells that are apoptotic was not influenced by co-expression of E1B-55kD (FIG. 13A and 13B). On the other hand, co-expression of E1B-21kD revealed a significant reduction of the apoptin-induced apoptosis in both Saos-2 and U2OS cells (FIGS. 13A and 13B). As shown in FIG. 13C, the inhibiting activity of E1B-21kD seems to be dose-dependent, but relatively low levels of E1B-21kD were already sufficient to obtain a significant inhibition. Western-blot analysis showed that the correct products of apoptin of 14kD and the E1B proteins of 55kD and 21kD were synthesized (FIG. 14).

Figure 15:
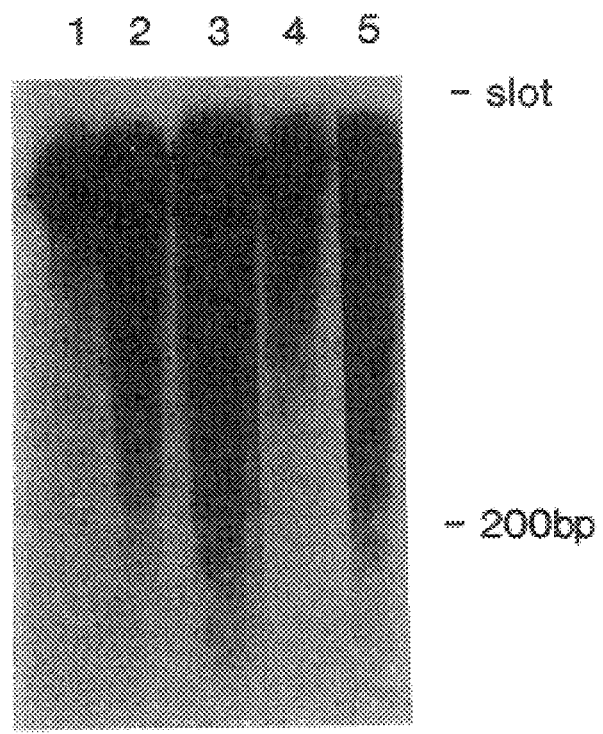
FIG. 15 shows the effect of expression of E1B proteins and Bcl-2 on the apoptin-induced DNA fragmentation in Saos-2 cells. Southern blot of DNA extracted from Saos-2 cells transfected with 21 ug plasmid pCMV-neo-Bam (lane 1), or co-transfected with 7 ug of plasmids pCMV-VP3 plus 14 ug of pCMV-neo-Bam (lane 2), pCMV-E1B55 (lane 3), pCMV-E1B21 (lane 4), or pCMV-Bcl2 (lane 5). The DNA was extracted and processed five days after transfection, as described in Example 6.

Five days after transfection, analysis of cellular DNA isolated from Saos-2 cells co-transfected with pCMV-VP3 and pCMV-neo-Bam or pCMV-E1B55 showed the classical apoptosis laddering of oligonucleosomal DNA. This specific DNA-degradation was significantly reduced in Saos-2 cells co-transfected with pCMV-VP3 and pCMV-E1B21, and almost absent in Saos-2 cells transfected with the control plasmid pCMV-neo-Bam (FIG. 15).

These data indicate that the p53-independent apoptotic pathway induced by apoptin in the analyzed human osteosarcoma cells can be inhibited by E1B-21kD but not by E1B-55kD.

Figures 14A, 14B, 14C:
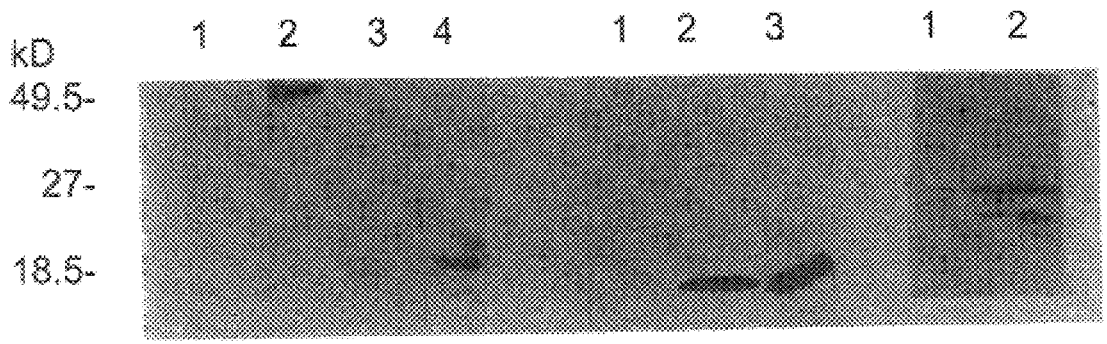
FIG. 14 shows a Western blot analysis of protein expression in transfected Saos-2 cells. Panel A. Expression of E1B-55kD and E1B-21kD in the presence of apoptin. Saos-2 cells were co-transfected with 7 ug of pCMV-VP3 and 14 ug of pCMV-neo-Bam (lanes 1 and 3), pCMV-E1B55 (lane 2), or pCMV-E1B21 (lane 4). The blots were stained with the E1B-55K-specific MAb 1G11 (lane 3 and 4). Panel B. Expression of E1B-21kD does not negatively influence the level of apoptin. Saos-2 cells were transfected with 21 ug of pCMV-neo-Bam (lane 1), or co-transfected with 7 ug of pCMV-VP3 and 14 ug of pCMV-neo-Bam (lane 2) or pCMV-E1B21 (lane 3). The blots were stained with the apoptin-specific MAb 85.1. Panel C. Expression of endogenous and exogenous human Bcl-2 in Saos-2 cells. Saos-2 cells were transfected with 7 ug of pCMV-VP3 and 14 ug of pCMV-neo-Bam (lane 1) or pCMV-Bcl2 (lane 2). The blot was stained with the Bcl-2 specific MAb Bcl-2 (100).

Cytoplasmic Retention of Apoptin Saos-2 and U2OS Cells by Co-Express of E1B-21kD To examine by which mechanism E1B-21kD negatively regulates the apoptin-induced apoptosis, we first analyzed the level of apoptin in Saos-2 cells co-transfected with pCMV-VP3 and pCMV-E1B21 or pCMV-neo-Bam. Western blot analysis revealed that the level of apoptin is similar in the presence or absence of E1B-21kD (FIG. 14B).

Figure 16A:
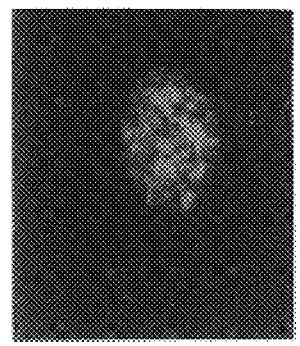
FIG. 16 shows indirect immunofluorescence and DAPI staining of Saos-2 cells co-transfected with 2.5 ug pCMV-VP3 DNA and 5 ug of pCMV-neo-Bam DNA (A and B) or pCMV-E1B21 (C, D, and E). The cells were fixed 48 h after transfection. Panels A and B, and panels C, D and E are representations of an identical cell. Panel A and C were stained with anti-apoptin MAb 85.1, panel D with anti-E1B-21kD MAb 1G11, and panel B and E with DAPI.
Figure 16B:
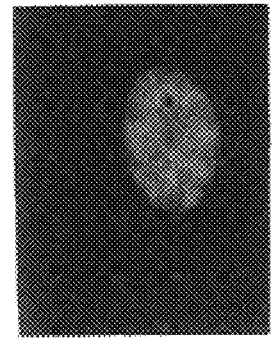
Figure 16C:
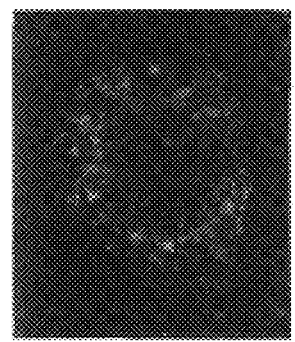
Figure 16D:
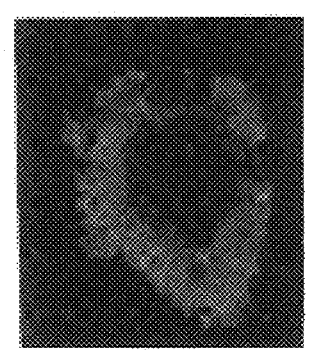
Figure 16E:
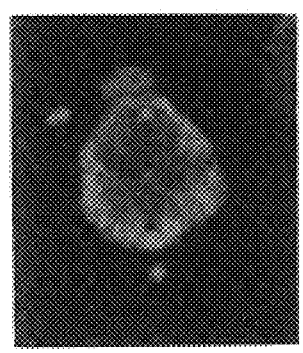

We observed previously that both early after CAV infection and after transfection of cells with plasmid encoding apoptin only, apoptin exhibits a fine granular distribution within the nucleus. At a later stage, it forms aggregates and the cells become apoptotic and their DNA is fragmented and condensed. In the present experiments early after transfection apoptin was fine-granularly located in the nucleus (in Saos-2 cells (FIG. 16A and 16B) and U2OS. In contrast, apoptin co-expressed with E1B-21kD in Saos-2 cells (FIG. 16C, 16D, and 16E) and U2OS cells, was found to co-localize mainly with E1B-21kD in the perinuclear region and only a minor part was located in the nucleus.

Therefore, E1B-21kD might inhibit apoptin-induced apoptosis in Saos-2 and U2OS cells by preventing apoptin to enter into the nucleus and/or to stay there.

Inhibition of Apoptin-induced Apoptosis Is Cell-Type-Dependent

Figure 17:
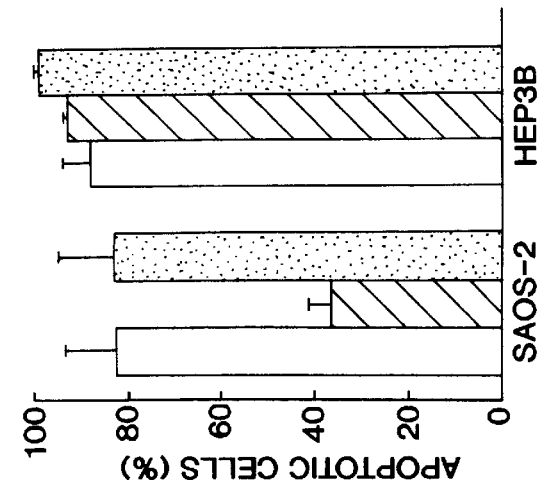
FIGS. 17 shows the effect of expression of E1B-21kD and Bcl-2 on the induction of apoptosis by apoptin in the p53 cell lines Saos-2 and Hep3B. The percentage given is that of the apoptin-positive cells which are apoptotic 6 days after transfection. The cells were co-transfected with 2.5 ug of pCMV-VP3 and 5 ug of pCMV-neo-Bam (open bars), 5 ug of pCMV-E1B21 (hatched bars), or pCMV-Bcl2 (dotted bars). At least 3 independent experiments were carried out. Per experiment at least 200 apoptin-positive cells were examined.

To investigate the generality of the inhibition of apoptin-induced apoptosis by E1B-21kD, we studied the effect of E1B-21kD expression on the level of apoptin-induced apoptosis in the p53 hepatoma cells Hep3B and the p53+ kidney rhabdoid tumor cells G401. The number of apoptin-expressing apoptotic cells was screened by indirect immunofluorescence and DAP1 or P1 staining. Surprisingly, at several timepoints after transfection the percentage of apoptin-expressing Hep 3B and G401 cells, which became apoptotic, was similar to the Hep3B and G401 cells containing both apoptin and E1B-21kD. For the sake of brevity, only the data of Hep3B cells at six days after transfection are given in FIG. 17. Transient expression of apoptin in G401/6.1 cells (stably transfected G401 cells expressing E1B-2kD) resulted also in a similar frequency of apoptosis induction as seen in parental G401 cells. In a parallel study, Saos-2 cells co-transfected with pCMV-VP3 and pCMV-neo-Bam or pCMV-E1B21 were found to reveal the E1B-21kD-specific inhibition of apoptin-induced apoptosis (FIG. 17). In agreement with our earlier hypothesis that activity of apoptin is highly dependent on its localization, immunofluorescence revealed that in Hep3B and G401 cells expression of E1B-21kD did not prevent apoptin from being located in the nucleus.

Bcl-2 Expression Does Not Inhibit Apoptosis Induced by Apoptin

In general, Bcl-2 has been found to be the cellular counterpart of E1B-21kD with regard to the inhibition of apoptosis (Chiou et al., (1994) J. Viral 68:6553–6566). We examined whether Bcl-2 could inhibit the apoptin-induced apoptosis similar to E1B-21kD. Firstly, we showed that plasmid pCMV-Bcl2 indeed expressed the human Bcl-2 product in transfected cells, Saos-2 cells in FIG. The endogenous Bcl-2expression was rather low, whereas after transfection the Bcl-2 product was clearly visible. The immunofluorescence data showed that endogenous Bcl-2 was expressed mainly during the mitotic stage and was located in the nucleus, whereas exogenous Bcl-2 did not vary significantly during the cell cycle and was located in the cytoplasm.

Saos-2 cells were co-transfected with pCMV-VP3 and pCMV-Bcl2, pCMV-neo-Bam as negative control, or pCMV-E1B21 as positive control. By immunofluorescence and P1-staining, we observed that co-expression of apoptin and Bcl-2 in Saos-2 cells caused the same level of apoptin-induced apoptosis as expression of apoptin only (FIG. 14C). Furthermore, expression of Bcl-2 could not prevent the apoptin-induced oligonucleosomal DNA laddering in Saos-2 cells (FIG. 15). In a parallel experiment, expression of E1B-21kD clearly inhibited the apoptin-induced apoptosis. In Hep3B cells Bcl-2 also did not inhibit the induction of apoptosis by apoptin (FIG. 17).

Figure 18B:
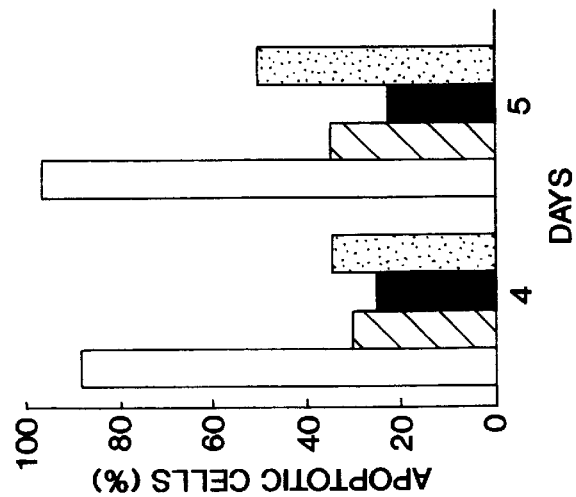
FIG. 18 shows the effect of expression of E1B-55kD, E1B-21kD, and Bcl-2 on the induction of apoptosis by p53 in Saos-2 (panel A) and Hep3B (panel B) cell lines. The cells were co-transfected with 2.5 ug of pCMV-p53 and 5 ug of pCMV-neo-Bam (open bars), pCMV-E1B21 (hatched bars), pCMV-E1B55 (closed bars), or pCMV-Bcl2 (dotted bars). Two independent transfections were carried out. The cells were analyzed 4 or 5 days after transfection. The percentage given is that of p53-positive cells which are apoptotic. Per experiment at least 200 p53-positive cells were examined.
Figure 18A:
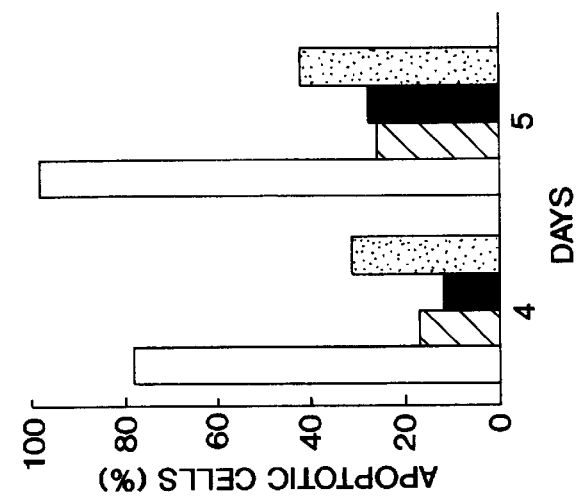

E1B-55kD, E1B-21kD, As Well As Bcl-2, Can Inhibit p53-Induced Apoptosis in Saos-2 and Hep3B Cells To illustrate that the E1B-21kD, E1b-55kD or Bcl-2 do have a biological effect in cells in which they cannot inhibit apoptin-induced apoptosis, we examined whether these three proteins could inhibit apoptosis caused by over-expression of p53 in both Saos-2 and Hep3B cells. Compared to co-transfection of these cells with pCMV-p53 and pCMV-neo-Bam, co-transfection with plasmids pCMV-p53 and pCMV-E1B55, pCMV-E1B21, or pCMV-Bcl2 resulted in a significant reduction of apoptosis induced by p53, as analyzed by immunofluorescence and P1-staining (FIG. 18). p53 co-located mainly with E1B-55K in discrete cytoplasmic bodies, whereas in the presence of E1B-21kD and Bcl-2 p53 was located in the nucleus. Thus, absence of effect of these proteins on apoptin-induced apoptosis can not be explained by non-functionality of the expressed proteins in these cells for they can inhibit the p53-induced apoptotic pathway.

In conclusion, the p53-dependent pathway seems to be distinct from the apoptin-induced p53-independent pathway in human tumor cells. The fact that in a large number of tumors apoptosis cannot be induced by a variety of chemo-therapeutic agents seems to be related to disrupted functions of p53. Therefore, induction of a p53-independent apoptotic pathway is a useful approach for tumor therapy.

Example 7

Reduction of Tumor or Formation Using CAV VP3
Expression of VP3 in stimulated primary human T cells Truncated VP3 was partially translocated from the nucleus to the cytoplasm and showed a reduced apoptotic activity as discussed infra. These results suggest that for optimal induction of apoptosis VP3 has to be directed to the nucleus.

Phytohemagglutinin-stimulated primary human T cells were transfected with plasmid pCMV-VP3 (Zhuang et al., (1995). The cells were fixed with 80% acetone. Immunofluorescence assays were carried out with a 100-fold dilution of the VP3-specific monoclonal antibody CVI-CAV-85.1 (85.1) and propidium-iodide, which stains apoptotic DNA weakly (Noteborn et al., (1992) J. Viral 65:3131–3139); Telford et al., (1992) Cytometry 13:137–143.

Expression Of VP3 In Mouse Tumor Cells In Vitro

We have also examined whether VP3 can induce apoptosis also in mammalian tumor cells of non-human origin. Therefore, cells of the mouse tumor cell line Crip (Danos (1988) Proc. Nat'l Acad. Sci. (USA) 85:6460–6464) were transfected with pCMV-VP3 DNA encoding VP3. Three days after transfection the cells were fixed. By means of immunofluorescence and propidium-iodide staining the cells were examined for expression of VP3, and whether they became apoptotic. Already, at three days after transfection 54% of the mouse tumor cells, which contain VP3, have become apoptotic. These results indicate that VP3 can induce apoptosis in different mammalian (tumor) cell lines.

In Hep 3B Cells VP3-induced Apoptotic Pathway Is Distinct From the p53-induced Apoptotic Pathway As demonstrated infra, VP3 induces apoptosis in osteosarcoma cells, without the presence of wild-type p53. We examined whether Ad 5 E1B21K protein and Bcl-2 can inhibit the p53-independent pathway of apoptosis induced by VP3 in comparison to p53-dependent apoptosis. To that end, we studied the effect of co-expression of these proteins with VP3 or p53 in the human hepatoma Hep3B cell line.

Hep3B cells were co-transfected with pCMV-VP3 and pCMV-neo-Bam DNA (negative control), pCMV-E1B21 DNA, encoding the Ad5 E1B21K protein or pCMV-Bcl2, encoding human Bcl-2. The number of VP3-expressing cells was screened by indirect immunofluorescence and by 2,4-diamidino-2-phenylindole staining, which is weak and/or irregular when the cells have become apoptotic.

Figure 19:
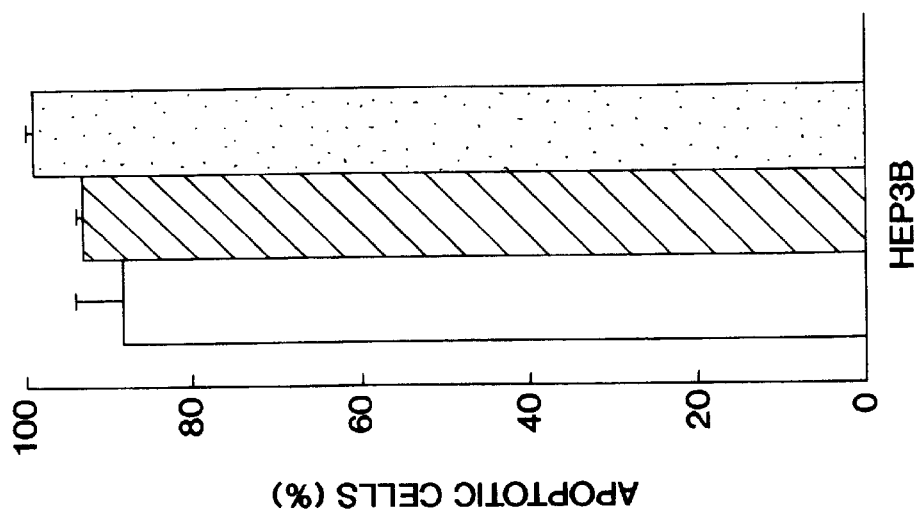
FIG. 19 shows the effect of expression of E1B-2lkD and Bcl-2 on the induction of apoptosis by VP3 in p53-minus Hep3B cells. The percentage given is that of the apoptin-positive cells which are apoptotic 6 days after transfection. The cells were co-transfected with 2.5 ug of pCMV-VP3 and 5 ug of PCMV-neo-Bam (open bars), 5 ug of pCMV-E1B21

Surprisingly, at several timepoints after transfection the percentage of apoptin-expressing Hep3B cells, which became apoptotic was similar to the Hep3B cells containing both VP3 and E1B-21K or both VP3 and Bcl-2. For the sake of brevity, only the data obtained six days after transfection are given in FIG. 19.

To illustrate that E1B-21K or Bcl-2 indeed have an anti-apoptotic effect in Hep3B cells, we examined whether these two proteins could inhibit apoptosis caused by over-expression of p53 in Hep3B cells. Compared to co-transfection of Hep3b cells with pCMV-p53 DNA encoding wild-type p53 (Baker et al., (1990) supra) and pCMV-neo-Bam, co-transfection with plasmids pCMV-p53 and pCMV-E1B21, or pCMV-Bcl2 resulted in a significant reduction of apoptosis induced by p53, as analyzed by immunofluorescence and propidium-iodide staining (FIG. 20).

Thus, absence of effect of E1B 21K and Bcl-2 proteins on VP3-induced apoptosis can not be explained by non-functionality of the expressed proteins in Hep3B cells for they can inhibit p53-induced apoptotic pathway. The fact that E1B 21K and Bcl2 still could negatively influence the p53-regulated apoptotic pathway in Hep3B cells, although the VP3-induced apoptosis could not be inhibited indicates that the p53-dependent and VP3-inducible p53-independent apoptotic pathway are distinct routes at least within Hep3B cells.

The fact that in a large number of tumors apoptosis cannot be induced by a variety of chemotherapeutic agents seems to be related to disrupted functions of p53. Therefore, induction of a p53-independent apoptotic pathway might be a useful approach as alternative candidate for tumor therapy.

As the case above results show, CAV protein VP3 is itself capable of inducing apoptosis in diverse human tumor cells. VP3 was expressed in various human hematologic malignant cell lines derived from leukemias and lymphoma. Three of these cell lines contain Bcl2 or BCR-ABL proteins, known to block apoptosis induced by chemotherapeutic compounds. By immunofluorescence and propidium-iodide straining VP3 was shown to induce apoptosis in all analyzed cell lines. Expression of VP3 in the human breast tumor cell line MCF-7 also resulted in the induction of apoptosis. VP3 also induces apoptosis in human osteosarcoma cells, regardless whether they expressed wild-type, mutant p53, or no p53 at all. The fact that VP3 can induce p53-independent apoptosis in human tumor cells and can overcome the block of apoptosis by Bcl-2 or BCR-ABL makes VP3 a potential candidate for treatment of frequently occurring types of cancer cells that do not contain p53 and/or enhanced levels of Bcl-2 or BCR-ABL. VP3 can be used in treatments for reducing tumor formation. These treatments may be based on the gene encoding VP3 or on the VP3 protein. Furthermore, the results provide evidence that expression of the CAV-specific protein VP2 or the expression both proteins VP3 and VP3 might also serve for the possible induction of cell death in tumor cells. The study of the stimulated human primary T cells revealed that VP3 accumulated mainly in their cytoplasm. Five days after transfection, not more than 20% of the VP3-positive cells became apoptotic. In comparison, transfection of plasmid DNA encoding VP3 in other hematologic cell lines, resulted in the induction of apoptosis of up to 95% of the VP3-positive cells (PCT/NL94/00168). These data suggest that apoptin might be less toxic for primary T cells than the analyzed human hematologic malignant cell lines.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now having been fully described, it will be apparent to one of ordinary skill in the art that many changes and modifications can be made thereto without departing from the spirit or scope of the appended claims.

What is claimed is:

1. A method of effecting apoptosis in tumor cells, said method comprising:
providing to said tumor cells a nucleotide sequence, derived from a Chicken Anemia Virus genome, that codes for a protein or fragment thereof that induces apoptosis, whereby, when said nucleotide sequence is expressed, apoptosis in said tumor cells is effected.

2. The method according to claim 1, wherein said protein is VP2 or VP3.

3. The method according to claim 1, wherein said protein has an amino acid sequence comprising amino acid residues 1 to 110 of the amino acid sequence shown in SEQ ID NO:7.

4. A method of effecting apoptosis in tumor cells, said method comprising:
providing to said tumor cells two nucleotide sequences, derived from a Chicken Anemia Virus genome, that code for proteins or fragments thereof that induces apoptosis, whereby, when said nucleotide sequences are expressed, apoptosis in said tumor cells is effected.

5. The method according to claim 4, wherein said proteins are VP3 and VP2.

6. The method according to claim 1 or claim 4, wherein said tumor cells are p53 negative.

7. The method according to claim 1 or claim 4, wherein said tumor cells contain enhanced Bcl-2 or BCR-ABL proteins.

* * * * *

UNITED STATES PATENT AND TRADEMARK OFFICE
CERTIFICATE OF CORRECTION

PATENT NO. :     5,981,502                           Page 1 of 2
ISSUE DATE :     November 9, 1999
INVENTOR(S):     M.H.M. Noteborn and G. Koch
TITLE:

It is certified that error appears in the above-identified patent and that said Letters Patent is hereby corrected as shown below:

On the title page:
In the Inventors section [75], "Matheus" should be --Mathieu--.
In the Abstract section [57], line 13, "apiece of DAN" should be --a piece of DNA--.
In Column 3, line 26, "(⊚)" should be --(●)--;
in line 27, "85. 1" should be --85.1--; and
in lines 28-29, "immunof-luorescent" should be --immuno-fluorescent--.
In Column 9, line 49, "Mal. Cell. Biol." should be --*Mol. Cell. Biol.*--; and
in line 52, "cel" should be --cell--.
In Column 10, line 31, "Gene$^2$" should be --*Gene*--; and
in line 34, "an" should be --and--.
In Column 12, line 67, "85. 1" should be --85.1--.
In Column 13, line 41-42, "immunop-eroxidase" should be --immuno-peroxidase--.
In Column 14, line 19, "G. Gen Virol." should be --*J. Gen. Virol.*--; and
in line 26, "ph" should be --pH--.
In Column 16, line 60, "85. 1" should be --85.1--.

UNITED STATES PATENT AND TRADEMARK OFFICE
CERTIFICATE OF CORRECTION

PATENT NO. : 5,981,502
DATED : November 9, 1999
INVENTOR(S) : M.H.M. Noteborn and G. Koch It is certified that error appears in the above-identified patent and that said Letters Patent is hereby corrected as shown below:

In Column 17, line 53, "Jobo-1" should be --Jobo-0--; and
in line 55, "85. 1" should be --85.1--.
In Column 18, line 40, "J. Viral" should be --*J. Virol*--; and
in lines 51-52, "dasEcoR1" should be --*EcoRI*--.
In Column 19, line 2, "Viral." should be --*Virol.*--;
in line 11, "J. Viral." should be --*J. Virol.*--;
in line 22, "P1" should be --PI-- and "DAP1" should be --DAPI--;
in line 34, "primed$^{32}$P" should be --primed $^{32}$P--; and
in line 57, "P1 or DAP1" should be --PI or DAPI--.
In Column 20, line 50, "DAP1 or P1" should be --DAPI or PI--.
In Column 21, line 5, "J. Viral" should be --*J. Virol.*--;
in line 20, "P1" should be --PI--; and
in line 42, "P1" should be --PI--.
In Column 22, line 5, "J. Viral" should be --*J. Virol.*--; and
in line 24, "Ad 5" should be --Ad5--.
In Column 42, line 28, "induces" should be --induce--.

Signed and Sealed this

Twelfth Day of September, 2000

Attest:

Q. TODD DICKINSON

*Attesting Officer*     *Director of Patents and Trademarks*

```
                          SEQUENCE LISTING (1) GENERAL INFORMATION:

(iii) NUMBER OF SEQUENCES: 29

(2) INFORMATION FOR SEQ ID NO: 1:

(i) SEQUENCE CHARACTERISTICS:
         (A) LENGTH: 16 base pairs
         (B) TYPE: nucleic acid
         (C) STRANDEDNESS: unknown
         (D) TOPOLOGY: unknown (ii) MOLECULE TYPE: DNA (genomic)

(iii) HYPOTHETICAL: NO (xi) SEQUENCE DESCRIPTION: SEQ ID NO: 1:

GATCCAACCC GGGTTG                                                       16

(2) INFORMATION FOR SEQ ID NO: 2:

(i) SEQUENCE CHARACTERISTICS:
         (A) LENGTH: 16 base pairs
         (B) TYPE: nucleic acid
         (C) STRANDEDNESS: unknown
         (D) TOPOLOGY: unknown (ii) MOLECULE TYPE: DNA (genomic)

(iii) HYPOTHETICAL: NO (xi) SEQUENCE DESCRIPTION: SEQ ID NO: 2:

AATTCAACCC GGGTTG                                                       16

(2) INFORMATION FOR SEQ ID NO: 3:

(i) SEQUENCE CHARACTERISTICS:
         (A) LENGTH: 449 amino acids
         (B) TYPE: amino acid
         (D) TOPOLOGY: unknown (ii) MOLECULE TYPE: protein (iii) HYPOTHETICAL: NO
```

(xi) SEQUENCE DESCRIPTION: SEQ ID NO: 3:

```
Met Ala Arg Arg Ala Arg Pro Arg Gly Arg Phe Tyr Ser Phe Arg
 1               5                  10                 15

Arg Gly Arg Trp His His Leu Lys Arg Leu Arg Arg Tyr Lys Phe
            20                  25                  30

Arg His Arg Arg Gln Arg Tyr Arg Arg Ala Phe Arg Lys Ala
            35                  40                  45

Phe His Asn Pro Arg Pro Gly Thr Tyr Ser Val Arg Leu Pro Asn Pro
        50                  55                  60

Gln Ser Thr Met Thr Ile Arg Phe Gln Gly Val Ile Phe Leu Thr Glu
 65                  70                  75                  80

Gly Leu Ile Leu Pro Lys Asn Ser Thr Ala Gly Gly Tyr Ala Asp His
                    85                  90                  95

Met Tyr Gly Ala Arg Val Ala Lys Ile Ser Val Asn Leu Lys Glu Phe
                100                 105                 110

Leu Leu Ala Ser Met Asn Leu Thr Tyr Val Ser Lys Ile Gly Gly Pro
            115                 120                 125

Thr Ala Gly Glu Leu Ile Ala Asp Gly Ser Lys Ser Gln Ala Ala Asp
    130                 135                 140

Asn Trp Pro Asn Cys Trp Leu Pro Leu Asp Asn Asn Val Pro Ser Ala
145                 150                 155                 160

Thr Pro Ser Ala Trp Trp Arg Trp Ala Leu Met Met Met Gln Pro Thr
                165                 170                 175

Asp Ser Cys Arg Phe Phe Asn His Pro Lys Gln Met Thr Leu Gln Asp
                180                 185                 190

Met Gly Arg Met Phe Gly Gly Trp His Leu Phe Arg His Ile Glu Thr
            195                 200                 205

Arg Phe Gln Leu Leu Ala Thr Lys Asn Glu Gly Ser Phe Ser Pro Val
    210                 215                 220

Ala Ser Leu Leu Ser Gln Gly Glu Tyr Leu Thr Arg Arg Asp Asp Val
225                 230                 235                 240

Lys Tyr Ser Ser Asp His Gln Asn Arg Trp Gln Lys Gly Gly Gln Pro
                245                 250                 255

Met Thr Gly Gly Ile Ala Tyr Ala Thr Gly Lys Met Arg Pro Asp Glu
            260                 265                 270

Gln Gln Tyr Pro Ala Met Pro Pro Asp Pro Ile Ile Thr Ala Thr
    275                 280                 285

Thr Ala Gln Gly Thr Gln Val Arg Cys Met Asn Ser Thr Gln Ala Trp
    290                 295                 300

Trp Ser Trp Asp Thr Tyr Met Ser Phe Ala Thr Leu Thr Ala Leu Gly
305                 310                 315                 320

Ala Gln Trp Ser Phe Pro Pro Gly Gln Arg Ser Val Ser Arg Arg Ser
                325                 330                 335

Phe Asn His His Lys Ala Arg Gly Ala Gly Asp Pro Lys Gly Gln Arg
                340                 345                 350

Trp His Thr Leu Val Pro Leu Gly Thr Glu Thr Ile Thr Asp Ser Tyr
                355                 360                 365

Met Ser Ala Pro Ala Ser Glu Leu Asp Thr Asn Phe Phe Thr Leu Tyr
    370                 375                 380

Val Ala Gln Gly Thr Asn Lys Ser Gln Gln Tyr Lys Phe Gly Thr Ala
385                 390                 395                 400

Thr Tyr Ala Leu Lys Glu Pro Val Met Lys Ser Asp Ala Trp Ala Val
                405                 410                 415
```

```
     Val Arg Val Gln Ser Val Trp Gln Leu Gly Asn Arg Gln Arg Pro Tyr
             420                 425                 430

Pro Asn Asp Val Asn Trp Ala Asn Ser Thr Met Tyr Trp Gly Thr Gln
             435                 440                 445

Pro
```

(2) INFORMATION FOR SEQ ID NO: 4:

(i) SEQUENCE CHARACTERISTICS:
        (A) LENGTH: 1348 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO: 4:

```
ATGGCAAGAC GAGCTCGCAG ACCGAGGCCG ATTTTACTCC TTCAGAAGAG GACGGTGGCA    60
CCACCTCAAG CGACTTCGAC GAAGATATAA ATTTCGACAT CGGAGGAGAC AGCGGTATCG   120
TAGACGAGCT TTTAGGAAGG CCTTTCACAA CCCCCGCCCC GGTACGTATA GTGTGAGGCT   180
GCCGAACCCC CAATCTACTA TGACTATCCG CTTCCAAGGG GTCATCTTTC TCACGGAAGG   240
ACTCATTCTG CCTAAAAACA GCACAGCGGG GGGCTATGCA GACCACATGT ACGGGGCGAG   300
AGTCGCCAAG ATCTCTGTGA ACCTGAAAGA GTTCCTGCTA GCCTCAATGA ACCTGACATA   360
CGTGAGCAAA ATCGGAGGCC CCATCGCCGG TGAGTTGATT GCGGACGGGT CTAAATCACA   420
AGCCGCGGAC AATTGGCCTA ATTGCTGGCT GCCGCTAGAT AATAACGTGC CCTCCGCTAC   480
ACCATCGGCA TGGTGGAGAT GGGCCTTAAT GATGATGCAG CCCACGGACT CTTGCCGGTT   540
CTTTAATCAC CCAAAGCAGA TGACCCTGCA AGACATGGGT CGCATGTTTG GGGGCTGGCA   600
CCTGTTCCGA CACATTGAAA CCCGCTTTCA GCTCCTTGCC ACTAAGAATG AGGGATCCTT   660
CAGCCCCGTG GCGAGTCTTC TCTCCCAGGG AGAGTACCTC ACGCGTCGCG ACGATGTTAA   720
GTACAGCAGC GATCACCAGA ACCGGTGGCA AAAAGGCGGA CAACCGATGA CGGGGGGCAT   780
TGCTTATGCG ACCGGGAAAA TGAGACCCGA CGAGCAACGA TACCCTGCTA TGCCCCCAGA   840
CCCCCCGATC ATCACCGCTA CTACAGCGCA AGGCACGCAA GTCCGCTGCA TGAATAGCAC   900
GCAAGCTTGG TGGTCATGGG ACACATATAT GAGCTTTGCA ACACTCACAG CACTCGGTGC   960
ACAATGGTCT TTTCCTCCAG GCAACGTTC AGTTTCTAGA CGGTCCTTCA ACCACCACAA  1020
GGCGAGAGGA GCCGGGGACC CCAAGGGCCA GAGATGGCAC ACGCTGGTGC CGCTCGGCAC  1080
GGAGACCATC ACCGACAGCT ACATGTCAGC ACCCGCATCA GAGCTGGACA CTAATTTCTT  1140
TACGCTTTAC GTAGCGCAAG GCACAAATAA GTCGCAACAG TACAAGTTCG GCACAGCTAC  1200
ATACGCGCTA AAGGAGCCGG TAATGAAGAG CGATGCATGG GCAGTGGTAC GCGTCCAGTC  1260
GGTCTGGCAG CTGGGTAACA GGCAGAGGCC ATACCCATGG GACGTCAACT GGGCGAACAG  1320
CACCATGTAC TGGGGACGC AGCCCTGA                                     1348
```

(2) INFORMATION FOR SEQ ID NO: 5:

(i) SEQUENCE CHARACTERISTICS:
        (A) LENGTH: 216 amino acids
        (B) TYPE: amino acid
        (D) TOPOLOGY: unknown (ii) MOLECULE TYPE: protein (iii) HYPOTHETICAL: NO (xi) SEQUENCE DESCRIPTION: SEQ ID NO: 5:

```
Met His Gly Asn Gly Gly Gln Pro Ala Ala Gly Gly Ser Glu Ser Ala
 1               5                  10                  15

Leu Ser Arg Glu Gly Gln Pro Gly Pro Ser Gly Ala Ala Gln Gly Gln
                20                  25                  30

Val Ile Ser Asn Glu Arg Ser Pro Arg Arg Tyr Ser Thr Arg Thr Ile
            35                  40                  45

Asn Gly Val Gln Ala Thr Asn Lys Phe Thr Ala Val Gly Asn Pro Ser
        50                  55                  60

Leu Gln Arg Asp Pro Asp Trp Tyr Arg Trp Asn Tyr Asn His Ser Ile
65                  70                  75                  80

Ala Val Trp Leu Arg Glu Cys Ser Arg Ser His Ala Lys Ile Cys Asn
                85                  90                  95

Cys Gly Gln Phe Arg Lys His Asn Phe Gln Glu Cys Ala Gly Leu Glu
                100                 105                 110

Asp Arg Ser Thr Gln Ala Ser Leu Glu Glu Ala Ile Leu Arg Pro Leu
            115                 120                 125

Arg Val Gln Gly Lys Arg Ala Lys Arg Lys Leu Asp Tyr His Tyr Ser
130                 135                 140

Gln Pro Thr Pro Asn Arg Lys Lys Ala Tyr Lys Thr Val Arg Trp Gln
145                 150                 155                 160

Asp Glu Leu Ala Asp Arg Glu Ala Asp Phe Thr Pro Ser Glu Glu Asp
                165                 170                 175

Gly Gly Thr Thr Ser Ser Asp Phe Asp Glu Asp Ile Asn Phe Asp Ile
            180                 185                 190

Gly Gly Asp Ser Gly Ile Val Asp Glu Leu Leu Gly Arg Pro Phe Thr
        195                 200                 205

Thr Pro Ala Pro Val Arg Ile Val
        210                 215
```

(2) INFORMATION FOR SEQ ID NO: 6:

(i) SEQUENCE CHARACTERISTICS:
        (A) LENGTH: 651 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO: 6:

```
ATGCACGGGA ACGGCGGACA ACCGGCCGCT GGGGGCAGTG AATCGGCGCT TAGCCGAGAG    60

GGGCAACCTG GGCCCAGCGG AGCCGCGCAG GGGCAAGTAA TTTCAAATGA ACGCTCTCCA   120

AGAAGATACT CCACCCGGAC CATCAACGGT GTTCAGGCCA CCAACAAGTT CACGGCCGTT   180

GGAAACCCCT CACTGCAGAG AGATCCGGAT TGGTATCGCT GGAATTACAA TCACTCTATC   240

GCTGTGTGGC TGCCCGAATG CTCGCGCTCC CACGCTAAGA TCTGCAACTG CGGACAATTC   300

AGAAAGCACT GGTTTCAAGA ATGTGCCGGA CTTGAGGACC GATCAACCCA AGCCTCCCTC   360

GAAGAAGCGA TCCTGCGACC CCTCCGAGTA CAGGGTAAGC GAGCTAAAAG AAAGCTTGAT   420

TACCACTACT CCCAGCCGAC CCCGAACCGC AAAAAGGCGT ATAAGACTGT AAGATGGCAA   480

GACGAGCTCG CAGACCGAGA GGCCGATTTT ACTCCTTCAG AAGAGGACGG TGGCACCACC   540

TCAAGCGACT TCGACGAAGA TATAAATTTC GACATCGGAG GAGACAGCGG TATCGTAGAC   600
```

GAGCTTTTAG GAAGGCCTTT CACAACCCCC GCCCCGGTAC GTATAGTGTG A          651

(2) INFORMATION FOR SEQ ID NO: 7:

(i) SEQUENCE CHARACTERISTICS:
        (A) LENGTH: 121 amino acids
        (B) TYPE: amino acid
        (D) TOPOLOGY: unknown (ii) MOLECULE TYPE: protein (iii) HYPOTHETICAL: NO (xi) SEQUENCE DESCRIPTION: SEQ ID NO: 7:

```
Met Asn Ala Leu Gln Glu Asp Thr Pro Pro Gly Pro Ser Thr Val Phe
 1               5                  10                  15

Arg Pro Pro Thr Ser Ser Arg Pro Leu Glu Thr Pro His Cys Arg Glu
            20                  25                  30

Ile Arg Ile Gly Ile Ala Gly Ile Thr Ile Thr Leu Ser Leu Cys Gly
            35                  40                  45

Cys Ala Asn Ala Arg Ala Pro Thr Leu Arg Ser Ala Thr Ala Asp Asn
50                  55                  60

Ser Glu Ser Thr Gly Phe Lys Asn Val Pro Asp Leu Arg Thr Asp Gln
65                  70                  75                  80

Pro Lys Pro Pro Ser Lys Lys Arg Ser Cys Asp Pro Ser Glu Tyr Arg
                85                  90                  95

Val Ser Glu Leu Lys Glu Ser Leu Ile Thr Thr Thr Pro Ser Arg Pro
                100                 105                 110

Arg Thr Ala Lys Arg Arg Ile Arg Leu
            115                 120
```

(2) INFORMATION FOR SEQ ID NO: 8:

(i) SEQUENCE CHARACTERISTICS:
        (A) LENGTH: 366 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO: 8:

ATGAACGCTC TCCAAGAAGA TACTCCACCC GGACCATCAA CGGTGTTCAG GCCACCAACA          60

AGTTCACGGC CGTTGGAAAC CCCTCACTGC AGAGAGATCC GGATTGGTAT CGCTGGAATT         120

ACAATCACTC TATCGCTGTG TGGCTGCGCG AATGCTCGCG CTCCCACGCT AAGATCTGCA         180

ACTGCGGACA ATTCAGAAAG CACTGGTTTC AAGAATGTGC CGGACTTGAG GACCGATCAA         240

CCCAAGCCTC CCTCGAAGAA GCGATCCTGC GACCCCTCCG AGTACAGGGT AAGCGAGCTA         300

AAAGAAAGCT TGATTACCAC TACTCCCAGC CGACCCCGAA CCGCAAAAAG GCGTATAAGA         360

CTGTAA                                                                   366

(2) INFORMATION FOR SEQ ID NO: 9:

(i) SEQUENCE CHARACTERISTICS:
        (A) LENGTH: 12 amino acids
        (B) TYPE: amino acid
        (D) TOPOLOGY: unknown (ii) MOLECULE TYPE: peptide (iii) HYPOTHETICAL: NO (xi) SEQUENCE DESCRIPTION: SEQ ID NO: 9:

Glu Asp Thr Pro Pro Gly Pro Ser Thr Val Phe Arg
                 1               5                  10

(2) INFORMATION FOR SEQ ID NO: 10:

(i) SEQUENCE CHARACTERISTICS:
                 (A) LENGTH: 12 amino acids
                 (B) TYPE: amino acid
                 (D) TOPOLOGY: unknown (ii) MOLECULE TYPE: peptide (iii) HYPOTHETICAL: NO (xi) SEQUENCE DESCRIPTION: SEQ ID NO: 10:

Asp Thr Pro Pro Gly Pro Ser Thr Val Phe Arg Pro
                 1               5                  10

(2) INFORMATION FOR SEQ ID NO: 11:

(i) SEQUENCE CHARACTERISTICS:
                 (A) LENGTH: 12 amino acids
                 (B) TYPE: amino acid
                 (D) TOPOLOGY: unknown (ii) MOLECULE TYPE: peptide (iii) HYPOTHETICAL: NO (xi) SEQUENCE DESCRIPTION: SEQ ID NO: 11:

Thr Pro Pro Gly Pro Ser Thr Val Phe Arg Pro Pro
                 1               5                  10

(2) INFORMATION FOR SEQ ID NO: 12:

(i) SEQUENCE CHARACTERISTICS:
                 (A) LENGTH: 12 amino acids
                 (B) TYPE: amino acid
                 (D) TOPOLOGY: unknown (ii) MOLECULE TYPE: peptide (iii) HYPOTHETICAL: NO (xi) SEQUENCE DESCRIPTION: SEQ ID NO: 12:

Pro Pro Gly Pro Ser Thr Val Phe Arg Pro Pro Thr
 1               5                  10

(2) INFORMATION FOR SEQ ID NO: 13:

(i) SEQUENCE CHARACTERISTICS:
                 (A) LENGTH: 12 amino acids
                 (B) TYPE: amino acid
                 (D) TOPOLOGY: unknown (ii) MOLECULE TYPE: peptide (iii) HYPOTHETICAL: NO (xi) SEQUENCE DESCRIPTION: SEQ ID NO: 13:

Pro Gly Pro Ser Thr Val Phe Arg Pro Pro Thr Ser
 1               5                  10

(2) INFORMATION FOR SEQ ID NO: 14:

(i) SEQUENCE CHARACTERISTICS:
                 (A) LENGTH: 12 amino acids (B) TYPE: amino acid
(D) TOPOLOGY: unknown (ii) MOLECULE TYPE: peptide (iii) HYPOTHETICAL: NO (xi) SEQUENCE DESCRIPTION: SEQ ID NO: 14:

Gly Pro Ser Thr Val Phe Arg Pro Pro Thr Ser Ser
1               5                   10

(2) INFORMATION FOR SEQ ID NO: 15:

(i) SEQUENCE CHARACTERISTICS:
    (A) LENGTH: 12 amino acids
    (B) TYPE: amino acid
    (D) TOPOLOGY: unknown (ii) MOLECULE TYPE: peptide (iii) HYPOTHETICAL: NO (xi) SEQUENCE DESCRIPTION: SEQ ID NO: 15:

Pro Ser Thr Val Phe Arg Pro Pro Thr Ser Ser Arg
1               5                   10

(2) INFORMATION FOR SEQ ID NO: 16:

(i) SEQUENCE CHARACTERISTICS:
    (A) LENGTH: 12 amino acids
    (B) TYPE: amino acid
    (D) TOPOLOGY: unknown (ii) MOLECULE TYPE: peptide (iii) HYPOTHETICAL: NO (xi) SEQUENCE DESCRIPTION: SEQ ID NO: 16:

Gln Glu Cys Ala Gly Leu Glu Asp Arg Ser Thr Gln
1               5                   10

(2) INFORMATION FOR SEQ ID NO: 17:

(i) SEQUENCE CHARACTERISTICS:
    (A) LENGTH: 12 amino acids
    (B) TYPE: amino acid
    (D) TOPOLOGY: unknown (ii) MOLECULE TYPE: peptide (iii) HYPOTHETICAL: NO (xi) SEQUENCE DESCRIPTION: SEQ ID NO: 17:

Glu Cys Ala Gly Leu Glu Asp Arg Ser Thr Gln Ala
1               5                   10

(2) INFORMATION FOR SEQ ID NO: 18:

(i) SEQUENCE CHARACTERISTICS:
    (A) LENGTH: 12 amino acids
    (B) TYPE: amino acid
    (D) TOPOLOGY: unknown (ii) MOLECULE TYPE: peptide (iii) HYPOTHETICAL: NO (xi) SEQUENCE DESCRIPTION: SEQ ID NO: 18:

Cys Ala Gly Leu Glu Asp Arg Ser Thr Gln Ala Ser
1               5                   10

(2) INFORMATION FOR SEQ ID NO: 19:

(i) SEQUENCE CHARACTERISTICS:
        (A) LENGTH: 12 amino acids
        (B) TYPE: amino acid
        (D) TOPOLOGY: unknown (ii) MOLECULE TYPE: peptide (iii) HYPOTHETICAL: NO (xi) SEQUENCE DESCRIPTION: SEQ ID NO: 19:

```
Ala Gly Leu Glu Asp Arg Ser Thr Gln Ala Ser Leu
 1               5                   10
```

(2) INFORMATION FOR SEQ ID NO: 20:

(i) SEQUENCE CHARACTERISTICS:
        (A) LENGTH: 12 amino acids
        (B) TYPE: amino acid
        (D) TOPOLOGY: unknown (ii) MOLECULE TYPE: peptide (iii) HYPOTHETICAL: NO (xi) SEQUENCE DESCRIPTION: SEQ ID NO: 20:

```
Gly Leu Glu Asp Arg Ser Thr Gln Ala Ser Leu Glu
 1               5                   10
```

(2) INFORMATION FOR SEQ ID NO: 21:

(i) SEQUENCE CHARACTERISTICS:
        (A) LENGTH: 12 amino acids
        (B) TYPE: amino acid
        (D) TOPOLOGY: unknown (ii) MOLECULE TYPE: peptide (iii) HYPOTHETICAL: NO (xi) SEQUENCE DESCRIPTION: SEQ ID NO: 21:

```
Pro Ser Thr Val Phe Arg Pro Pro Thr Ser Ser Arg
 1               5                   10
```

(2) INFORMATION FOR SEQ ID NO: 22:

(i) SEQUENCE CHARACTERISTICS:
        (A) LENGTH: 12 amino acids
        (B) TYPE: amino acid
        (D) TOPOLOGY: unknown (ii) MOLECULE TYPE: peptide (iii) HYPOTHETICAL: NO (xi) SEQUENCE DESCRIPTION: SEQ ID NO: 22:

```
Ser Thr Val Phe Arg Pro Pro Thr Ser Ser Arg Pro
 1               5                   10
```

(2) INFORMATION FOR SEQ ID NO: 23:

(i) SEQUENCE CHARACTERISTICS:
        (A) LENGTH: 12 amino acids
        (B) TYPE: amino acid
        (D) TOPOLOGY: unknown (ii) MOLECULE TYPE: peptide (iii) HYPOTHETICAL: NO (xi) SEQUENCE DESCRIPTION: SEQ ID NO: 23:

Thr Val Phe Arg Pro Pro Thr Ser Ser Arg Pro Leu
 1               5                  10

(2) INFORMATION FOR SEQ ID NO: 24:

(i) SEQUENCE CHARACTERISTICS:
        (A) LENGTH: 12 amino acids
        (B) TYPE: amino acid
        (D) TOPOLOGY: unknown (ii) MOLECULE TYPE: peptide (iii) HYPOTHETICAL: NO (xi) SEQUENCE DESCRIPTION: SEQ ID NO: 24:

Val Phe Arg Pro Pro Thr Ser Ser Arg Pro Leu Glu
 1               5                  10

(2) INFORMATION FOR SEQ ID NO: 25:

(i) SEQUENCE CHARACTERISTICS:
        (A) LENGTH: 12 amino acids
        (B) TYPE: amino acid
        (D) TOPOLOGY: unknown (ii) MOLECULE TYPE: peptide (iii) HYPOTHETICAL: NO (xi) SEQUENCE DESCRIPTION: SEQ ID NO: 25:

Phe Arg Pro Pro Thr Ser Ser Arg Pro Leu Glu Thr
 1               5                  10

(2) INFORMATION FOR SEQ ID NO: 26:

(i) SEQUENCE CHARACTERISTICS:
        (A) LENGTH: 12 amino acids
        (B) TYPE: amino acid
        (D) TOPOLOGY: unknown (ii) MOLECULE TYPE: peptide (iii) HYPOTHETICAL: NO (xi) SEQUENCE DESCRIPTION: SEQ ID NO: 26:

Arg Pro Pro Thr Ser Ser Arg Pro Leu Glu Thr Pro
 1               5                  10

(2) INFORMATION FOR SEQ ID NO: 27:

(i) SEQUENCE CHARACTERISTICS:
        (A) LENGTH: 12 amino acids
        (B) TYPE: amino acid
        (D) TOPOLOGY: unknown (ii) MOLECULE TYPE: peptide (iii) HYPOTHETICAL: NO (xi) SEQUENCE DESCRIPTION: SEQ ID NO: 27:

Pro Pro Thr Ser Ser Arg Pro Leu Glu Thr Pro His
 1               5                  10

(2) INFORMATION FOR SEQ ID NO: 28:

(i) SEQUENCE CHARACTERISTICS:
        (A) LENGTH: 25 base pairs
        (B) TYPE: nucleic acid
        (C) STRANDEDNESS: unknown -continued (D) TOPOLOGY: unknown (ii) MOLECULE TYPE: DNA (genomic)

(iii) HYPOTHETICAL: NO (xi) SEQUENCE DESCRIPTION: SEQ ID NO: 28:

AGCTTGATTA CCACTACTCC CTGAG                           25

(2) INFORMATION FOR SEQ ID NO: 29:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO: 29:

TCGACTCAGG GAGTAGTGGT AATCA                           25